US009228981B2

(12) United States Patent
    Jauriqui

(10) Patent No.: US 9,228,981 B2
(45) Date of Patent: Jan. 5, 2016

(54) RESONANCE INSPECTION-BASED SURFACE DEFECT SYSTEM/METHOD

(71) Applicant: Vibrant Corporation, Albuquerque, NM (US)

(72) Inventor: Leanne Jauriqui, Albuquerque, NM (US)

(73) Assignee: VIBRANT CORPORATION, Albuquerque, NM (US)

( * ) Notice: Subject to any disclaimer, the term of this patent is extended or adjusted under 35 U.S.C. 154(b) by 352 days.

(21) Appl. No.: 13/679,141

(22) Filed: Nov. 16, 2012

(65) Prior Publication Data
    US 2013/0269435 A1    Oct. 17, 2013

Related U.S. Application Data

(60) Provisional application No. 61/561,129, filed on Nov. 17, 2011.

(51) Int. Cl.
    *G01N 29/12*    (2006.01)
    *G01N 29/04*    (2006.01)

(52) U.S. Cl.
    CPC .............. *G01N 29/12* (2013.01); *G01N 29/041* (2013.01); *G01N 2291/103* (2013.01); *G01N 2291/265* (2013.01); *G01N 2291/2696* (2013.01)

(58) Field of Classification Search
    CPC ..... G01N 29/12; G01N 29/348; G01N 29/42; G01N 29/46; G01N 2291/014; G01N 2291/0423
    USPC .............................. 73/579, 587, 623, 648, 659
    See application file for complete search history.

(56) References Cited

U.S. PATENT DOCUMENTS

| 5,062,296 A | 11/1991 | Migliori |
| 5,257,544 A * | 11/1993 | Khuri-Yakub et al. ......... 73/579 |
| 5,351,543 A * | 10/1994 | Migliori et al. ................. 73/579 |
| 5,355,731 A | 10/1994 | Dixon et al. |
| 5,425,272 A | 6/1995 | Rhodes et al. |
| 5,631,423 A * | 5/1997 | Rhodes .......................... 73/579 |
| 5,837,896 A * | 11/1998 | Rhodes et al. .................. 73/579 |
| 7,649,632 B2 | 1/2010 | Murray |
| 8,368,289 B2 | 2/2013 | Karabutov et al. |
| 2006/0027021 A1 | 2/2006 | Choi et al. |

(Continued)

OTHER PUBLICATIONS

L. J. Hunter et al.: "Advances in Resonance Based NDT for Ceramic Components", AIP Conference Proceedings, vol. 1430, Jul. 17, 2011-Jul. 22, 2011, pp. 1137-1144.

(Continued)

*Primary Examiner* — Laura Martin
*Assistant Examiner* — Rose M Miller
(74) *Attorney, Agent, or Firm* — Marsh Fischmann & Breyfogle LLP

(57) ABSTRACT

A system and method for evaluating a part-under-test (120) is disclosed. The part-under-test (120) is excited using at least one drive frequency. A first surface acoustical wave (SAW) mode (206) is identified in the frequency response (200). A separate reference peak (204) for the identified SAW mode (206) is also identified in the frequency response (200). At least one degeneracy assessment zone (208) is evaluated for existence of a surface defect trigger condition. If a surface defect trigger condition exists, the part-under-test (120) may be rejected. Otherwise, the part-under-test (120) may be accepted.

21 Claims, 14 Drawing Sheets

(56) References Cited

U.S. PATENT DOCUMENTS

2011/0238336 A1 9/2011 Di Scalea et al.
2012/0330569 A1 12/2012 Singh et al.

OTHER PUBLICATIONS

Hsieh C P et al.: "One-Point Contact Measurement of Spherical Resonances", Applied Physics Letters, AIP, American Institute of Physics, Melville, NY, US, vol. 62, No. 24, Jun. 14, 1993, pp. 3091-3093.

Hsieh C P et al.: "Surface Defect Inspection of Spherical Objects by the Resonant Sphere Technique", Applied Physics Letters, AIP, American Institute of Physics, Melville, NY, US, vol. 60, No. 15, Apr. 13, 1992, pp. 1815-1817.

\* cited by examiner

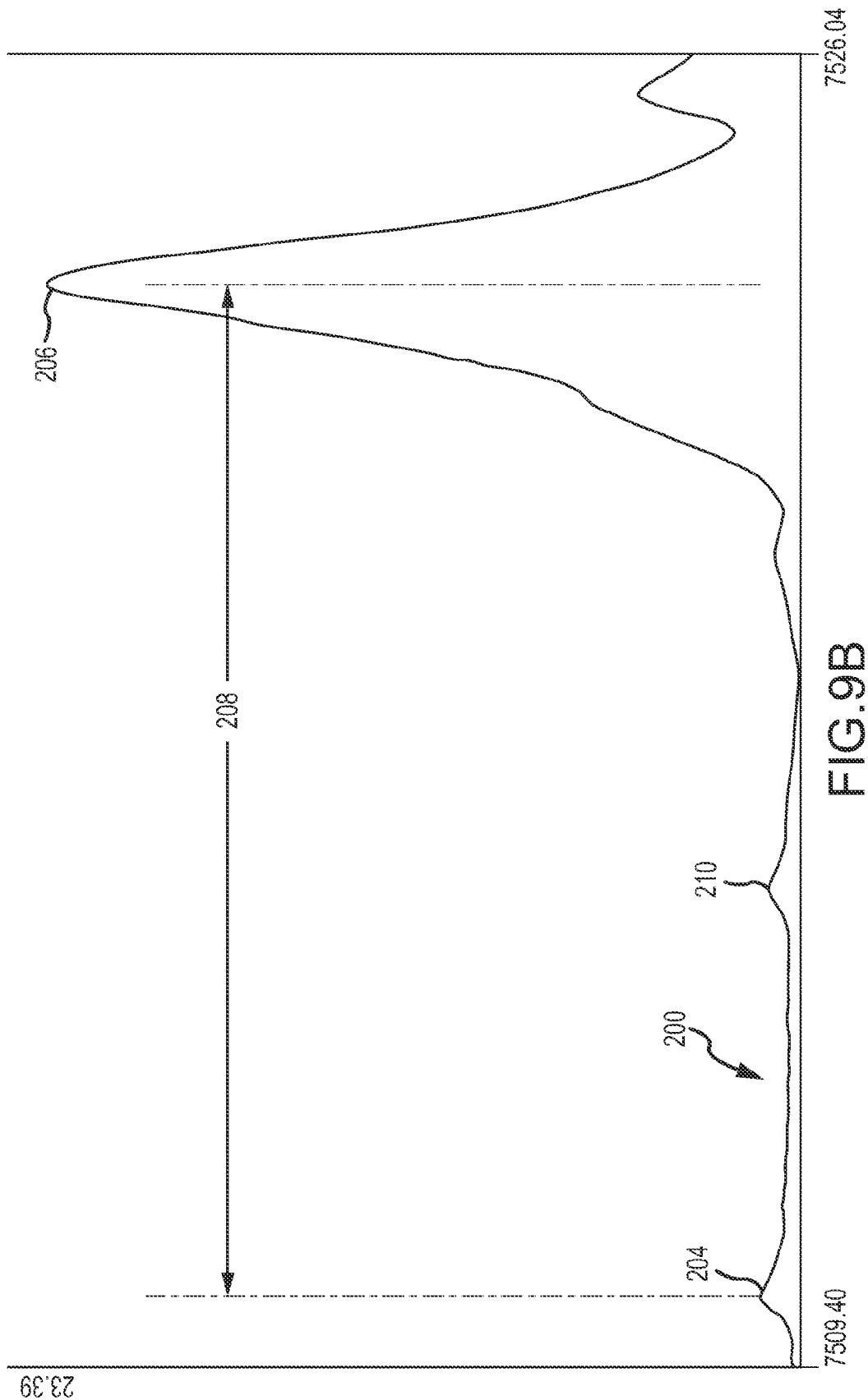

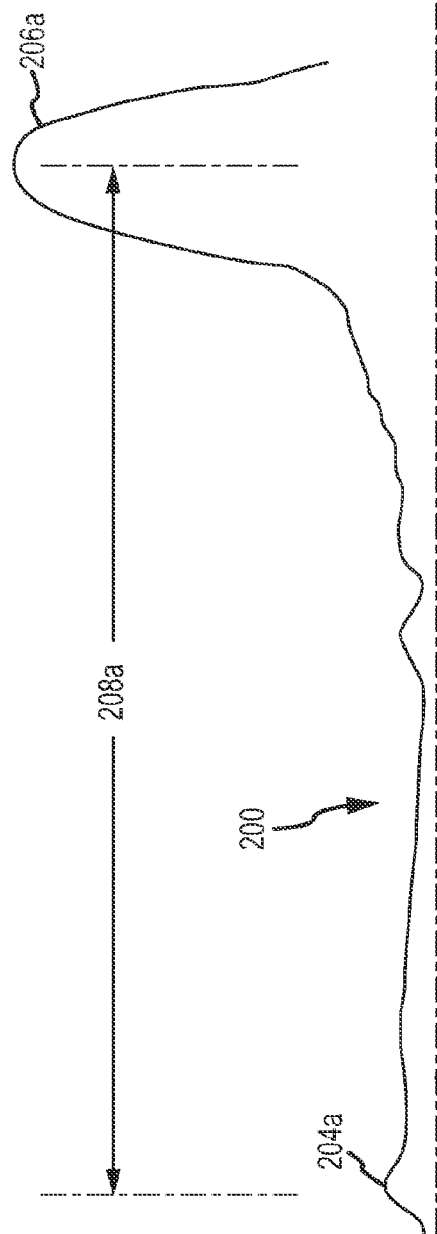
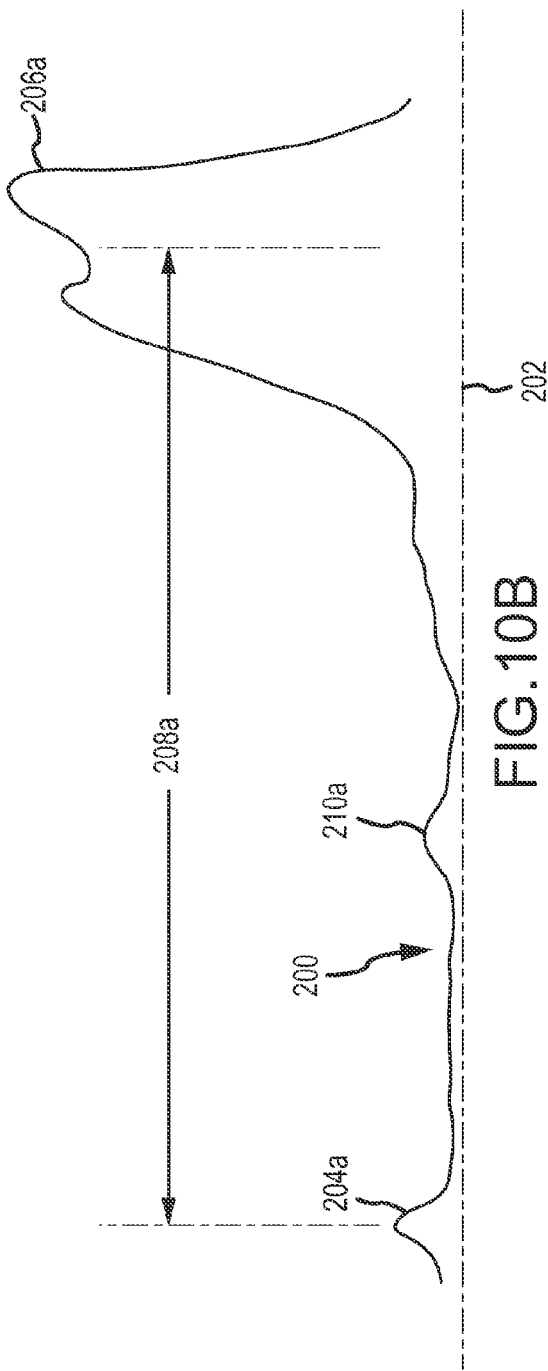
FIG. 10A
FIG. 10B

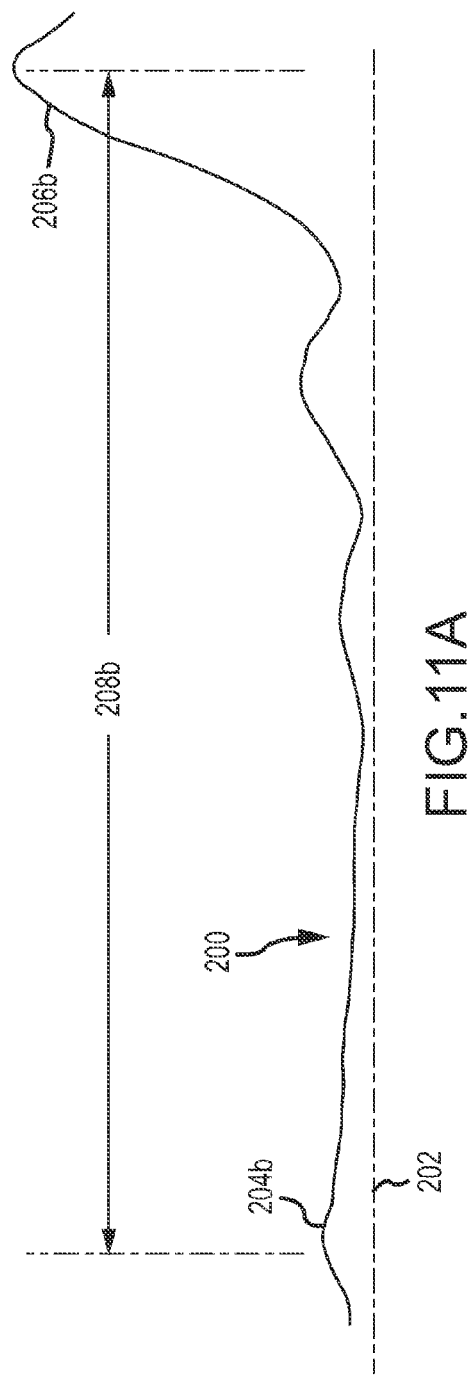
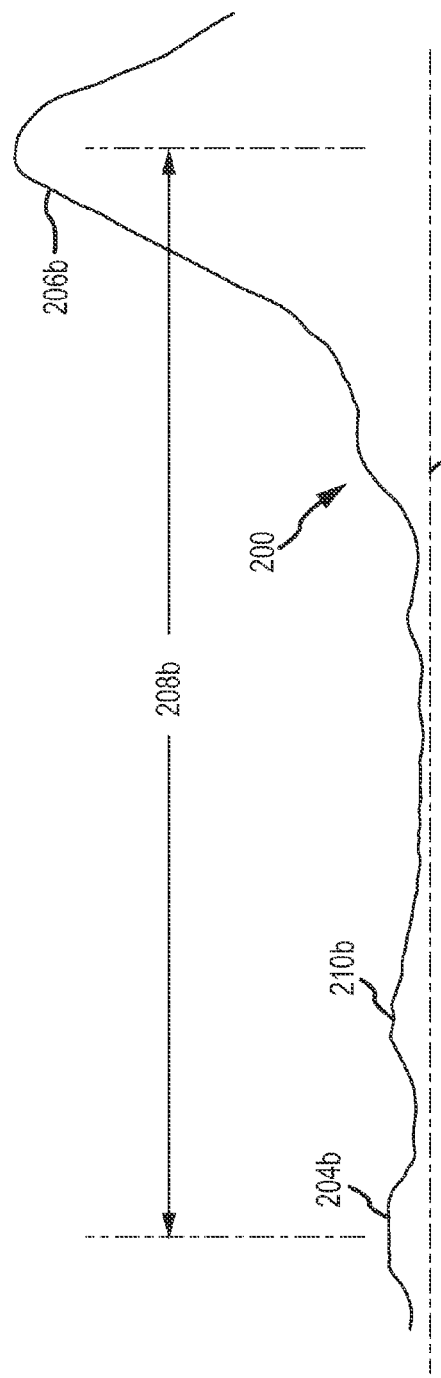
FIG. 11A
FIG. 11B

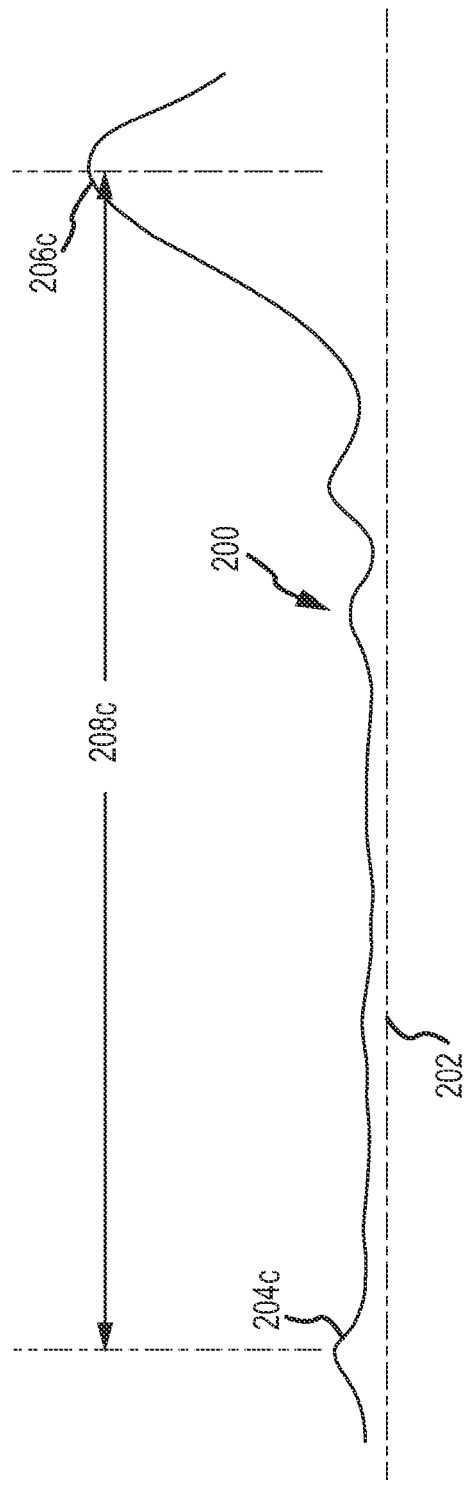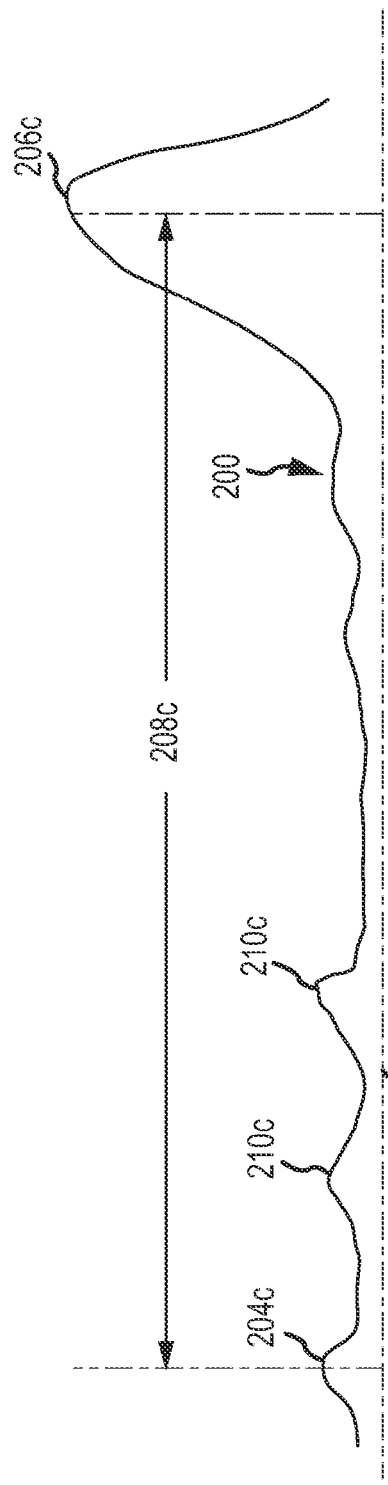

RESONANCE INSPECTION-BASED SURFACE DEFECT SYSTEM/METHOD

CROSS-REFERENCE TO RELATED APPLICATIONS

This patent application is a conversion of, and claims priority to, U.S. Provisional Patent Application Ser. No. 61/561,129 that is entitled "RESONANCE INSPECTION-BASED SURFACE DEFECT SYSTEM/METHOD," that was filed on 17 Nov., 2011, and the entire disclosure of which is hereby incorporated by reference in its entirety herein.

STATEMENTS REGARDING FEDERALLY SPONSORED RESEARCH OR DEVELOPMENT

The U.S. Government has a nonexclusive, nontransferable, irrevocable, paid-up license to practice, or have practiced for or on its behalf, the subject invention throughout the world as provided for by the terms of Contract Number N68335-09-C-0159 awarded by Naval Air Warfare Center AD (LKE).

FIELD OF THE INVENTION

The present invention generally relates to the testing of parts for surface defects and, more particularly, to using one or more SAW modes in the assessment of a part for surface defects.

BACKGROUND OF THE INVENTION

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

A first aspect of the present invention is embodied by an evaluation of a part for the existence of one or more surface defects. A part-under-test is excited using at least one input frequency. A first surface acoustical wave (SAW) mode is identified in a frequency response of the part-under-test to this excitation. A first reference peak is also identified in this same frequency response. A first zone (e.g., a degeneracy assessment zone) is characterized as extending between and including the first SAW mode and the first reference peak. The part-under-test is characterized as being defective based upon the development or an existence of a surface defect trigger condition. At least part of an existing surface defect trigger condition is satisfied from the first zone (e.g., the first zone at least makes a contribution to the satisfaction of the surface defect trigger condition).

A number of feature refinements and additional features are applicable to the first aspect of the present invention. These feature refinements and additional features may be used individually or in any combination. The following discussion is applicable to the first aspect, up to the start of the discussion of a second aspect of the present invention.

The surface defect trigger condition may be in the form of having at least one degenerate peak condition in the frequency response. At least one degenerate peak condition will exist within the first zone if the surface defect trigger condition does indeed exist. The surface defect trigger condition could be satisfied entirely from the first zone. However, one or more degenerate peak conditions may exist within other degeneracy assessment zones of the frequency response and could contribute to the satisfaction of the surface defect trigger condition. The surface defect trigger condition may be characterized as having a predetermined number (e.g., one or more) degenerate peak conditions within the frequency response of the part-under-test to the excitation of the part-under-test, but where at least one degenerate peak condition exists within the first zone.

The assessment of the first zone may include assessing for an existence of a spacing threshold between the first reference peak and a first degenerate peak within the first zone. A degenerate peak condition may be equated with this spacing threshold existing between the first reference peak and a first degenerate peak within the first zone. In one embodiment, the spacing threshold is satisfied only when the first degenerate peak is within a predetermined distance of the first reference peak (e.g., the spacing threshold may be in the form of the maximum spacing from the first reference peak that can exist in order for a given peak to be characterized as defining a degenerate peak condition).

The assessment of the first zone may include assessing for an existence of a spacing threshold between the first reference peak and each of at least two different degenerate peaks within the first zone. A degenerate peak condition may be equated with the spacing threshold existing between the first reference peak and each of at least two different degenerate peaks within the first zone. In one embodiment, the spacing threshold is satisfied only when each of at least two different degenerate peaks within the first zone is within a predetermined distance of the first reference peak (e.g., the spacing threshold may be in the form of the maximum spacing from the first reference peak that can exist in order for a given peak to be characterized as defining a degenerate peak condition).

The assessment of the first zone may include assessing for an existence of a spacing threshold between first and second degenerate peaks within the first zone. A degenerate peak condition may be equated with the spacing threshold existing between the first and second degenerate peaks within the first zone. In one embodiment, the spacing threshold is satisfied only when the first and second degenerate peaks are within a predetermined distance of each other (e.g., the spacing threshold may be in the form of the maximum spacing between a pair of peaks that can exist in order for this pair of peaks to be characterized as defining a degenerate peak condition).

The assessment of the first zone may include assessing for an existence of a spacing threshold between the first SAW mode and a first degenerate peak within the first zone. A degenerate peak condition may be equated with the spacing threshold existing between the first SAW mode and the first degenerate peak within the first zone. In one embodiment, the spacing threshold is satisfied only when the first SAW mode and the first degenerate peak are separated by at least a predetermined distance (e.g., the spacing threshold may be in the form of the minimum spacing that must exist between the first SAW mode and a given peak in order for this peak to be characterized as defining a degenerate peak condition).

Multiple degeneracy assessment zones may be evaluated in relation to the first aspect, including where the surface defect trigger condition may be satisfied collectively from multiple zones. A second surface acoustical wave (SAW) mode may be identified in the frequency response of the part-under-test that is produced by its excitation. A second reference peak may also be identified in this same frequency response. A second zone (e.g., another degeneracy assessment zone) may be characterized as extending between and including the second SAW mode and the second reference peak. The first and second zones may be completely independent of one another (e.g., non-overlapping). At least part of an existing surface defect trigger condition may be satisfied from the first and second zones (e.g., each of the first and second zones may make at least some contribution to the satisfaction of the surface defect trigger condition). The surface defect trigger condition may be in the form of each of the first and second zones having at least one degenerate peak condition.

The assessment of the first and second zones may include assessing for an existence of a spacing threshold between the first reference peak and a first degenerate peak within the first zone, and assessing for an existence of this same spacing threshold between the second reference peak and a second degenerate peak within the second zone. A degenerate peak condition may be equated with the spacing threshold existing between the first reference peak and the first degenerate peak within the first zone. A degenerate peak condition may be equated with the spacing threshold existing between the second reference peak and the second degenerate peak within the second zone. In one embodiment, the spacing threshold for the first zone is satisfied only when the first reference peak is within a predetermined distance of the first degenerate peak, and the spacing threshold for the second zone is satisfied only when the second reference peak is within this same predetermined distance of the second degenerate peak (e.g., the spacing threshold may be in the form of the maximum spacing from a given reference peak that can exist in order for a given peak in its zone to be characterized as defining a degenerate peak condition).

The assessment of the first and second zones may include assessing for an existence of a spacing threshold between the first reference peak and at least two different degenerate peaks within the first zone, as well as assessing for an existence of this same spacing threshold between the second reference peak and at least two different degenerate peaks within the second zone. A degenerate peak condition may be equated with this spacing threshold existing between the first reference peak and each of at least two different degenerate peaks within the first zone. A degenerate peak condition may be equated with this spacing threshold existing between the second reference peak and each of at least two different degenerate peaks within the second zone. In one embodiment, the spacing threshold is satisfied for the first zone only when each of at least two different degenerate peaks within the first zone is within a predetermined distance of the first reference peak, and the spacing threshold is satisfied for the second zone only when each of at least two different degenerate peaks within the second zone is within this same predetermined distance of the second reference peak (e.g., the spacing threshold may be in the form of the maximum spacing from a given reference peak that can exist in order for a given peak in its zone to be characterized as defining a degenerate peak condition).

The assessment of the first and second zones may include assessing for an existence of a spacing threshold between first and second degenerate peaks within the first zone, and assessing for an existence of this same spacing threshold between third and fourth degenerate peaks within the second zone. A degenerate peak condition for the first zone may be equated with a spacing threshold existing between the first and second degenerate peaks within the first zone. A degenerate peak condition for the second zone may be equated this same spacing threshold existing between the third and fourth degenerate peaks within the second zone. In one embodiment, the spacing threshold is satisfied for the first zone only when the first and second degenerate peaks within the first zone are within a predetermined distance of each other, and the spacing threshold is satisfied for the second zone only when the third and fourth degenerate peaks within the second zone are within this same predetermined distance of each other (e.g., the spacing threshold may be in the form of the maximum spacing between a pair of peaks in a common zone that can exist in order for this pair of peaks to be characterized as defining a degenerate peak condition).

The assessment of the first and second zones may include assessing for an existence of a spacing threshold between the first SAW mode and a first degenerate peak within the first zone, and assessing for an existence of this same spacing threshold between the second SAW mode and a second degenerate peak within the second zone. A degenerate peak condition may be equated with the threshold spacing existing between the first SAW mode and the first degenerate peak within the first zone. A degenerate peak condition may be equated with this same threshold spacing existing between the second SAW mode and the second degenerate peak within the second zone. In one embodiment, the spacing threshold is satisfied for the first zone only when the first SAW mode and the first degenerate peak are within a predetermined distance of each other, and is satisfied for the second zone only when the second SAW mode and the second degenerate peak are within this same predetermined distance of each other (e.g., the spacing threshold may be in the form of a minimum spacing that must exist between a SAW mode and a given peak in its zone in order for this peak to be characterized as defining a degenerate peak condition).

A second aspect of the present invention is embodied by an evaluation of a part for the existence of one or more surface defects. A part-under-test is excited at each of a plurality of input frequencies. Multiple surface acoustical wave (SAW) modes are identified in a frequency response of the part-under-test to this excitation. A separate reference peak is identified in this same frequency response for each of the SAW modes to be encompassed by the assessment. Multiple zones (e.g., degeneracy assessment zones) are assessed, with each zone extending from and including one of the SAW modes and its corresponding reference peak. The part-under-test is characterized as being defective based upon the development or an existence of a surface defect trigger condition.

A number of feature refinements and additional features are applicable to the second aspect of the present invention. These feature refinements and additional features may be used individually or in any combination. The following discussion is applicable to at least this second aspect. The noted "surface defect trigger condition" may be where the plurality of assessment zones collectively have a predetermined number of degenerate peak conditions. One or more degenerate peak conditions may exist in one or more of the zones, one or more zones may lack any surface degenerate peak condition, or both, and still satisfy the surface defect trigger condition.

Any number of zones may be assessed for purposes of the second aspect. A single zone could be assessed for purposes of determining whether or not a surface defect trigger condition exists. Less than all of the zones in the frequency response could be assessed for purposes of determining whether or not a surface defect trigger condition exists. All of the zones in the frequency response could be assessed for purposes of determining whether or not a surface defect trigger condition exists.

A degenerate peak condition may be characterized as the satisfaction of a spacing threshold between a degenerate peak within a given zone and its corresponding reference peak (the reference peak that defines one boundary of the zone occupied by this particular degenerate peak). In one embodiment, this spacing threshold is satisfied only when a degenerate peak (within a given zone) is within a predetermined distance of its corresponding reference peak (the reference peak that defines one boundary of the zone occupied by this particular degenerate peak). The spacing threshold may be in the form of the maximum spacing from a reference peak that can exist in order for a given peak within the same zone to be characterized as defining a degenerate peak condition.

A degenerate peak condition may be characterized as the satisfaction of a spacing threshold between two or more degenerate peaks within a given, common zone and their corresponding reference peak (the reference peak that defines one boundary of the common zone occupied by these particular degenerate peaks). In one embodiment, this spacing threshold is satisfied only when two or more degenerate peaks (within a given, common zone) are each within a predetermined distance of their corresponding reference peak (the reference peak that defines one boundary of the zone occupied by these particular degenerate peaks). The spacing threshold may be in the form of the maximum spacing from a reference peak that can exist in order for a given peak within the same zone to be characterized as defining a degenerate peak condition.

A degenerate peak condition may be characterized as the satisfaction of a spacing threshold between a pair of degenerate peaks within a given, common zone. In one embodiment, this spacing threshold is satisfied only when a pair of degenerate peaks (within a given, common zone) are within a predetermined distance of each other. The spacing threshold may be in the form of the maximum spacing between a pair of peaks that can exist in order for this pair of peaks to be characterized as defining a degenerate peak condition.

A degenerate peak condition may be characterized as the satisfaction of a spacing threshold between a given degenerate peak within a given zone and its corresponding SAW mode (the SAW mode that defines one boundary of the zone occupied by this particular degenerate peak). In one embodiment, this spacing threshold is satisfied only when a given degenerate peak (within a given zone) is within a predetermined distance of its corresponding SAW mode (the SAW mode that defines one boundary of the zone occupied by this particular degenerate peak). The spacing threshold may be in the form of the minimum spacing that must exist between a SAW mode and a given peak in its zone in order for this peak to be characterized as defining a degenerate peak condition.

A number of feature refinements and additional features are separately applicable to each of above-noted first and second aspects of the present invention. These feature refinements and additional features may be used individually or in any combination in relation to each of the first and second aspects. The present invention may be used to determine whether the part-under-test includes at least one surface defect (the present invention does not require that the number and/or location of one or more surface defects be identified). The part-under-test for purposes of the present invention may be of a symmetrical configuration. Representative configurations for a part-under-test for purposes of the present invention include without limitation a ball, sphere, cylinder, tapered roller, right circular cylinder, and the like.

The frequency response may be in the form of a plot of a collection of responses of the part-under-test at each frequency that may be used to drive the part-under-test. For instance, if the part-under-test is driven at frequency $f_1$, the amplitude of the response of the part-under-test at this same frequency $f_1$ may be included in the noted plot at the frequency $f_1$; if the part-under-test is driven at frequency $f_2$, the amplitude of the response of the part-under-test at this same frequency $f_2$ may be included in the plot at the frequency $f_2$; if the part-under-test is driven at frequency $f_3$, the amplitude of the response of the part-under-test at this same frequency $f_3$ may be included in the plot at this frequency $f_3$; and so forth. Once this plot is generated, one or more SAW modes and a corresponding reference peak may be identified in the plot, and one of more of the zones extending between a SAW mode and its corresponding reference peak may be assessed for purposes of determining if a surface defect trigger condition exists.

A surface acoustical wave (SAW) mode may be identified in a frequency response (to the excitation of the part-under-test) in any appropriate manner in relation to the present invention. The frequency at which a given SAW mode should appear may be determined mathematically. Another option is to determine the interval between SAW modes at a particular input frequency to a part, and to use this information to identify the SAW mode(s) of interest in the frequency response to the excitation of the part-under-test.

A reference peak for defining one boundary of a degeneracy assessment zone may be of any appropriate type, including a resonance peak. Such a resonance peak should remain in an at least substantially fixed position in a frequency response, whether the part-under-test is free from any surface defects or whether the part-under-test includes one or more surface defects of any appropriate type (e.g., surface damage on the part-under-test).

Each degeneracy assessment zone extends between and includes a reference peak and its corresponding SAW mode. A degeneracy assessment zone may be characterized as lacking any SAW mode other than the SAW mode that defines one of its boundaries (the other boundary being defined by a reference peak). A degeneracy assessment zone may lack an intermediate SAW mode between the reference peak and SAW mode that defines its two end boundaries. In one embodiment, the reference peak boundary for a given degeneracy assessment zone is at a lower frequency than the SAW mode that defines its other boundary.

Any spacing threshold that is used to determine whether or not a degenerate peak condition exists may be of any appropriate value. Any spacing threshold that is used to determine whether or not a degenerate peak condition exists may be implemented in any appropriate manner. One option is for a default spacing threshold to be made available (e.g., "hardwired" into a surface defect assessment module). Another option is to allow user input to establish a spacing threshold (e.g., via at least one data input device of any appropriate type that is operatively connected with a surface defect assessment module). Both a default spacing threshold option and a user inputted spacing threshold option could be made available for a given surface defect assessment of the part-under-test.

Original equipment manufacturer or OEM parts may be evaluated using the present invention. Non-OEM parts may also be evaluated using the present invention, for instance for purposes of determining whether a non-OEM part complies with an OEM part or other control group (of one or more other parts and/or part specifications).

The part-under-test may be in the form of an in-service part. An in-service part may be characterized as a part that has been released from production for use in one or more end-use applications. An "in-service part" in the context of the present invention encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part may be incorporated by an appropriate assembly or system (e.g., a turbine blade (an in-service part) in a jet engine (an assembly or system)).

The present invention may be used to evaluate new production parts (e.g., the part-under-test may be a new production part). A new production part may be characterized as a newly manufactured part that has not yet been released from production (e.g., parts that have not yet been shipped for use by an end user or customer). New production parts include parts that may have undergone at least some post-production testing of any appropriate type (including without limitation a surface defect inspection in accordance with the present invention and/or a resonance inspection).

The various aspects of the present invention each may be implemented as a method and/or as an inspection system or tool. In the case of an inspection system or tool, a surface defect assessment module may be configured to execute the assessments noted herein (e.g., such a surface defect assessment module may be configured to identify reference peaks and/or SAW modes in the frequency response, to is assess one or more zones for the existence of one or more degenerate peak conditions, and/or to assess for the existence/satisfaction of a surface defect trigger condition), and the part-under-test may be excited and the frequency response may be obtained in accordance with any one or more of the following configurations.

An inspection of the part-under-test for purposes of the present invention may utilize a first transducer that excites or drives the part-under-test at multiple frequencies (e.g., by sweeping through a predetermined range of frequencies in any appropriate manner), along with at least one other transducer that measures the frequency response of this part-under-test to such excitations or drive frequencies (e.g., thereby encompassing using two "receiver" transducers). Any number of frequencies may be used to excite the part-under-test for the inspection, and the excitation frequencies may be input to the part-under-test in any appropriate pattern and for any appropriate duration. Another option is to use a single transducer for performing an inspection of the part-under-test. In this case, a transducer may drive the part-under-test at a certain frequency for a certain amount of time, and thereafter this same transducer may be used to obtain the frequency response of the part-under-test (e.g., after terminating the driving of the transducer at an input frequency). This may be repeated for multiple input or drive frequencies.

Any appropriate combination of excitation or drive frequencies may be used for an inspection in accordance with the present invention. Each transducer that is used to perform an inspection may be of any appropriate size, shape, configuration, and/or type. Although an inspection in accordance with the present invention could possibly be performed in situ (e.g., with the part in an installed condition or state), such an inspection will more typically be performed prior to installing a part for its end-use application or with the part being in an uninstalled condition or state.

An inspection of the part-under-test in accordance with the present invention may include using at least one transducer that excites the part-under-test through a range of frequencies, and using at least two other transducers to measure the frequency response of the part-under-test. Another option for an inspection of the part-under-test is to use a first transducer that excites the part-under-test at a number of different frequencies, and using this same transducer to measure the frequency response of the part-under-test.

An inspection in accordance with the present invention may include exciting the part-under-test using at least one drive transducer that is in contact with the part-under-test. Another option for an inspection in the case of the present invention is to excite the part-under-test using at least one drive transducer that is maintained in spaced relation to the part-under-test throughout the inspection. In one embodiment, such a drive transducer (e.g., a drive transducer that is spaced from the part-under-test for the inspection) may be in the form of a laser.

An inspection of the part-under-test in accordance with the present invention may entail obtaining a frequency response of this part using at least one receive transducer that is in contact with the part-under-test. Another option for this inspection is to obtain a frequency response of the part-under-test using at least one receive transducer that is maintained in spaced relation to this part-under-test. In one embodiment, a receive transducer used in the inspection of the part-under-test is in the form of a laser. The inspection of the part-under-test may include obtaining a frequency response of this part-under-test using laser vibrometry. The frequency response of the part-under-test in this case may be obtained from a single location using laser vibrometry. Another option for this case is to obtain the frequency response of the part-under-test by laser scanning multiple locations on the surface of this part-under-test.

Both a surface defect inspection and a resonance inspection may be undertaken in relation to the part-under test. The same "raw data" may be used for each of these inspections. The data analysis for each of these inspections may be undertaken at any appropriate time (e.g., simultaneously; sequentially and in any order; overlapping).

A resonance inspection may include exciting a part-under-test at a plurality of input frequencies and obtaining a frequency response of the part-under-test (e.g., to acquire/assess resonance data). A resonance inspection may be characterized as obtaining a whole body frequency response of the part-under-test using a number of different drive or input frequencies. In any case, the frequency response from the inspection of the first part-under-test may be compared with a resonance standard of any appropriate type when a resonance inspection of the part-under-test is conducted (in conjunction with a surface defect inspection as described herein). Such a resonance standard may be stored on a computer-readable storage medium. For instance, the resonance standard may be stored on a hard drive, disk drive, optical drive, flash drive, or the like, that is utilized by a computer for making the comparison. In any case, the comparison of the frequency response from a resonance inspection of the part-under-test with the resonance standard may utilize at least one processor (e.g., one or more processors of any appropriate type, where multiple processors may be integrated/implemented to define any appropriate processing architecture). In one embodiment, the resonance standard is equated with at least certain resonance attributes of a new production part. In another embodiment, the resonance standard is equated with at least certain resonance attributes of a normally aging of a part.

The resonance standard, against which the frequency response from a resonance inspection of the part-under-test may be compared, may be of any appropriate type and/or defined in any appropriate manner. One embodiment has this resonance standard including spectra (e.g., a "snapshot" of the whole body frequency response of a part at one or more points in time) of at least one other part. Another embodiment has this resonance standard being in the form of a mathematical model (e.g., resonance inspection results generated from software based upon projections/predictions).

The resonance standard which may be used in conjunction with the present invention may be based upon resonance inspection data from a single part or a population of parts. In one embodiment, the population of parts does not include the part-under-test. In any case, the resonance standard may be in the form of one or more representative spectra (e.g., one spectra for each of a plurality of parts that are part of the noted population). A given representative spectra may also be in the form of an average of spectra from each of the plurality of parts that are included within the noted population. The resonance standard may also be in the form of spectra from a single member of the population.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system utilizes "a frequency response transducer" alone does not mean that the resonance inspection system utilizes only a single frequency response transducer). Moreover, any failure to use phrases such as "at least one" also does not limit the corresponding feature to the singular (e.g., indicating that a resonance inspection system utilizes "a frequency response transducer" alone does not mean that the resonance inspection system utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

BRIEF DESCRIPTION OF THE FIGURES

FIG. 9B illustrates an enlarged view of a representative degeneracy assessment zone that may exist in the frequency response of FIG. 9A.

FIG. 10A is an enlarged view of a representative degeneracy assessment zone in a frequency response, and that may be characterized by the surface defect assessment module of FIG. 3 as lacking any degenerate peaks.

FIG. 10B is an enlarged view of the same degeneracy assessment zone from FIG. 10A, and that may be characterized by the surface defect assessment module of FIG. 3 as including one degenerate peak.

FIG. 11A is an enlarged view of a representative degeneracy assessment zone in a frequency response, and that may be characterized by the surface defect assessment module of FIG. 3 as lacking any degenerate peaks.

FIG. 11B is an enlarged view of the same degeneracy assessment zone from FIG. 11A, and that may be characterized by the surface defect assessment module of FIG. 3 as including one degenerate peak.

FIG. 12A is an enlarged view of a representative degeneracy assessment zone in a frequency response, and that may be characterized by the surface defect assessment module of FIG. 3 as lacking any degenerate peaks.

FIG. 12B is an enlarged view of the same degeneracy assessment zone from FIG. 12A, and that may be characterized by the surface defect assessment module of FIG. 3 as including two degenerate peaks.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
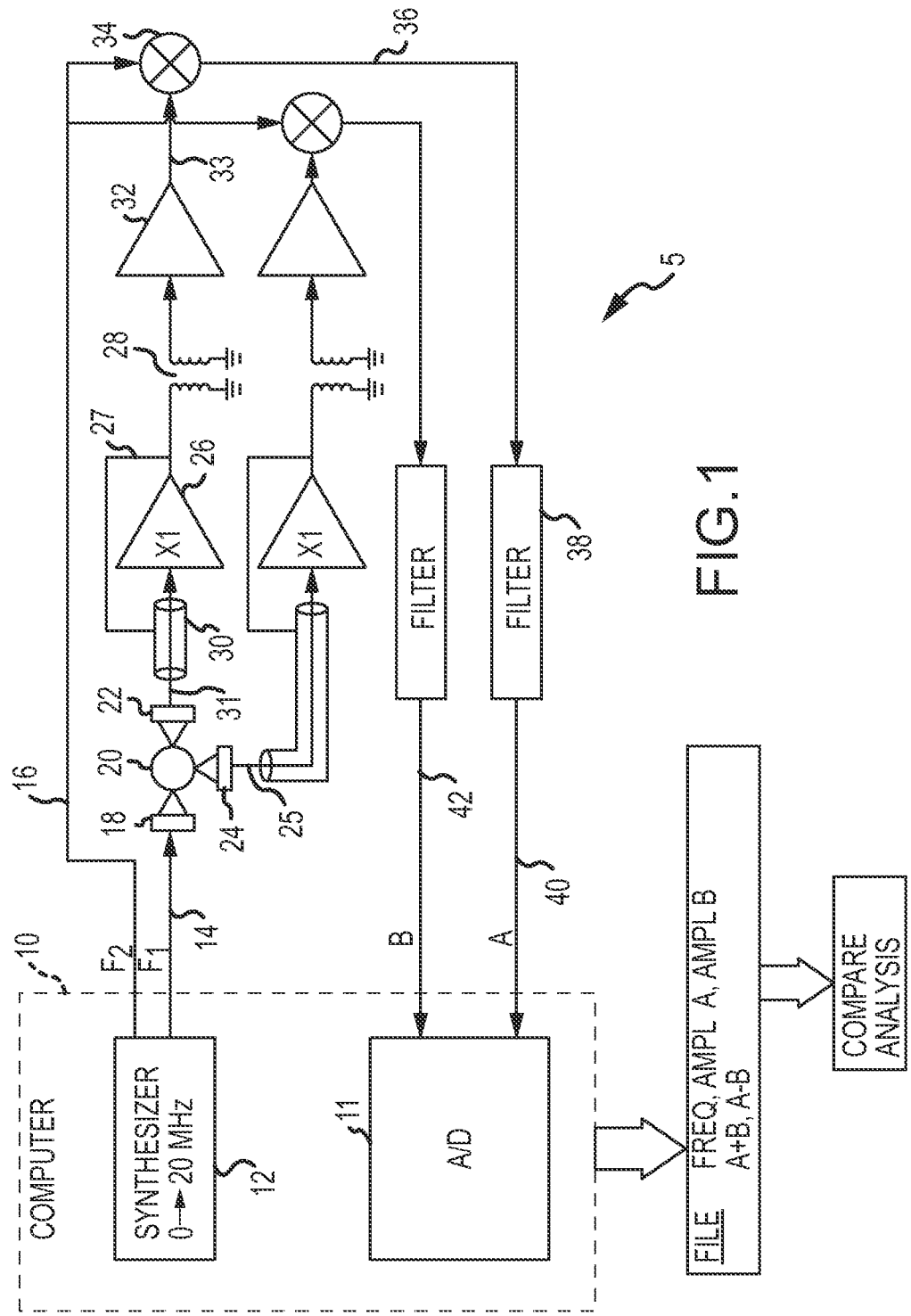
FIG. 1 is a block-diagram of one embodiment of a resonance inspection tool.
Figure 2:
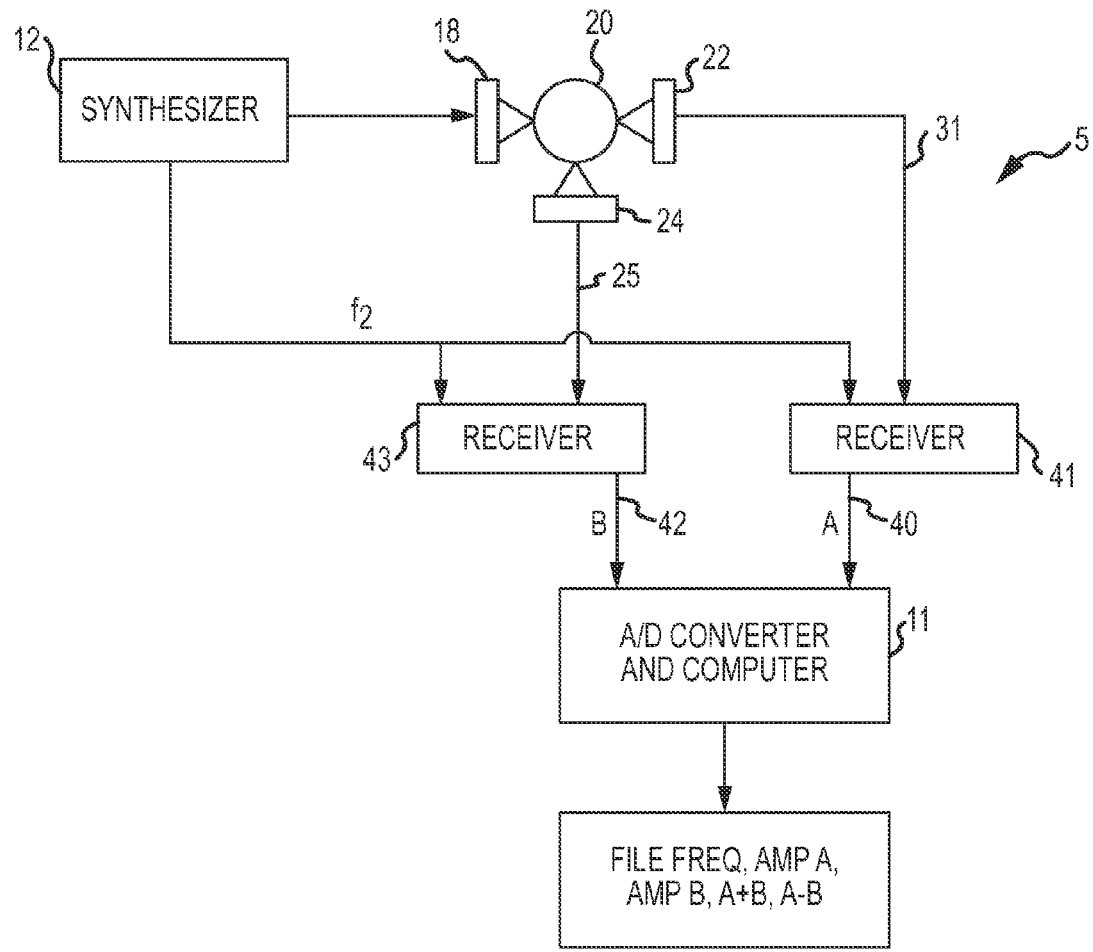
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and A/D converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present and step 66 stops the program. Once information is entered into file, subsequent processing can be used to generate a signature or characterize the object 20 such as the resonant magnitudes, the sum of resonant magnitudes, the difference of resonant magnitudes, or other manipulations of the multiple channel multiple frequency measurement which is used to perform the unique signature of the object 20. The magnitude of the outputs at each sensor location for each resonance frequency may be compared.

Figure 3:
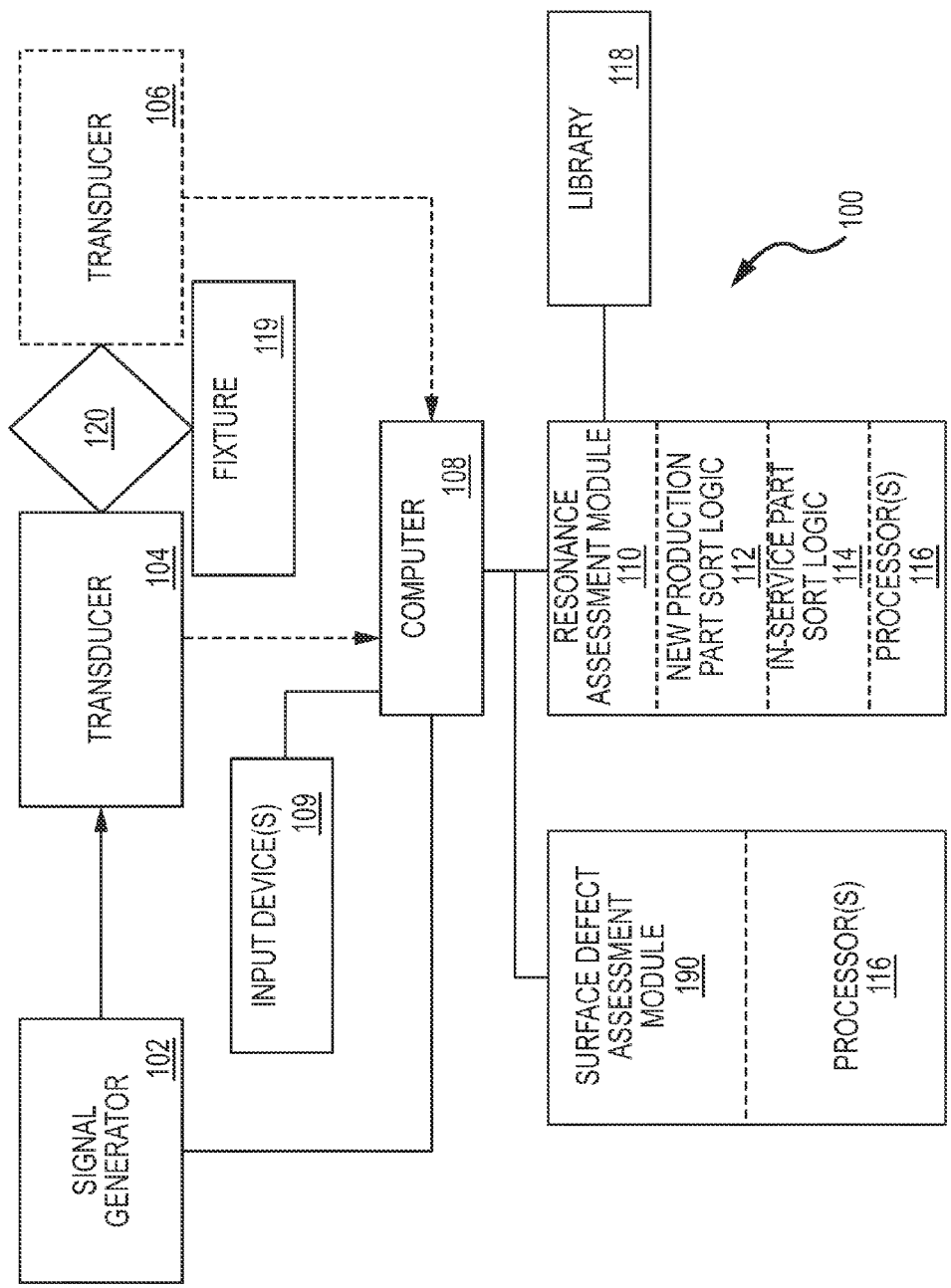
FIG. 3 is a block-diagram of one embodiment of an inspection tool that accommodates both a resonance inspection and a surface defect inspection.

Another embodiment of an inspection tool or system is illustrated in FIG. 3 and is identified by reference numeral 100. The inspection tool 100 may be used to assess a part or part-under-test (PUT) 120. This part-under-test 120 may be retained in a fixture 119 in any appropriate manner for execution of one or more inspections. Two different types of inspections may be undertaken using the configuration of the tool 100 shown in FIG. 3. The tool 100 may include a resonance assessment module 110 for performing a resonance inspection of the PUT 120. The tool 100 may include a surface defect assessment module 190 for performing a surface inspection of the PUT 120. Either one or both of these modules 110, 190 may be utilized by the tool 100. Both modules 110, 190 may entail driving the PUT 120 at one or more input frequencies and then assessing the frequency response of the PUT 120. The surface defect to assessment module 190 may be used to identify only surface defects in the PUT 120. The resonance assessment module 110 may be used to identify at least the existence of defects anywhere within the PUT 120.

The inspection tool 100 includes a signal generator 102 of any appropriate type, at least one transducer (e.g., transducer 104), and a computer 108. The transducer 104 may be of any appropriate type. In one embodiment, the transducer 104 is in physical contact with the PUT 120 to acquire data for the inspection of the PUT 120, and in this case may be characterized as being part of the fixture 119 for the PUT 120. Another embodiment has the transducer 104 being maintained in spaced relation to the PUT 120 to acquire data for the inspection of the PUT 120 (e.g., a laser, such as Nd:YAG lasers, TEA $CO_2$ lasers, excimer lasers, or diode lasers).

A PUT 120 that is analyzed or assessed by the inspection tool 100 may be of any appropriate size, shape, configuration, type, and/or class. For purposes of the inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part also may be incorporated by an assembly or system (e.g., a turbine blade (an in-service part) in a jet engine (an assembly or system)).

The signal generator 102 generates signals that are directed to the transducer 104 for transmission to the PUT 120 in any appropriate manner/fashion (e.g., via physical contact between the transducer 104 and the PUT 120; through a space between the transducer 104 and the PUT 120). Signals provided to the transducer 104 by the signal generator 102 are used to mechanically excite the PUT 120 (e.g., to provide energy to the PUT 120 for purposes of inducing vibration). Multiple frequencies may be input to the PUT 120 through the transducer 104 in any appropriate manner. This may be characterized as "sweeping" through a range of frequencies that are each input to the PUT 120, and this may be done in any to appropriate manner for purposes of the inspection tool 100. Any appropriate number/range of frequencies may be utilized, and any appropriate way of progressing through a plurality of frequencies (e.g., a frequency range) may be utilized by the inspection tool 100.

In one embodiment, at least one other transducer 106 is utilized in the inspection of the part PUT using the inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the PUT 120. It may be such that the PUT 120 is in fact entirely supported by the transducer 104 and any additional transducers 106 (e.g., the drive transducer 104 and one or more receive transducers 106 may define the fixture 119). Each transducer 106 that is utilized by the inspection tool 100 is used to acquire the frequency response of the PUT 120 to the frequencies input to the PUT 120 by the drive transducer 104, and therefore each transducer 106 may be characterized as an output or receiver transducer 106.

One or more transducers 106 utilized by the inspection tool 100 may be maintained in physical contact with the part 120 throughout the acquisition of data for an inspection. Another option is for one or more of the transducers 106 to be maintained in spaced relation with the part 120 throughout the acquisition of data for an inspection. A transducer 106 in the form of a laser may be maintained in spaced relation with the part throughout the acquisition of data for an inspection, and may be utilized to obtain the frequency response, of the PUT 120. Representative lasers that may be utilized as a transducer 106 by the inspection system 100 include without limitation Nd:YAG lasers, TEA $CO_2$ lasers, excimer lasers, or diode lasers. In one embodiment, the frequency response of the PUT 120 is acquired by laser vibrometry utilizing at least one transducer 106. A given transducer 106 in the form of a laser may acquire data on the PUT 120 from a single location, or a given transducer 106 in the form of a laser could acquire data on the PUT 120 by scanning the laser over multiple locations on the PUT 120.

Another embodiment of the inspection tool 100 of FIG. 3 utilizes only the transducer 104. That is, no additional transducers 106 are utilized by the inspection tool 100 in this case, and therefore the transducer 106 is presented by dashed lines in FIG. 3. In this case, the transducer 104 is used to input a drive signal to the PUT 120 (e.g., to excite the PUT 120 at a plurality of different frequencies), and is also used to acquire the frequency response of the PUT 120 to these input drive frequencies. Representative configurations for this drive/receive transducer configuration 104 include without limitation piezoceramic, piezocomposites, piezoelectric quartz crystal, and other electromechanical materials.

In the above-noted drive/receive transducer configuration 106, a first drive signal at a first frequency (from the signal generator 102) may be transmitted to the PUT 120 through the transducer 104, the transmission of this first drive signal may be terminated, and the transducer 104 may be used to acquire a first frequency response of the PUT 120 to this first drive signal (including while a drive signal is being transmitted to the PUT 120). The signal generator 102 may also be used provide a second drive signal at a second frequency to the transducer 104, which in turn transmits the second drive signal to the PUT 120, the transmission of this second drive signal may be terminated, and the transducer 104 may once again be used to acquire a second frequency response of the PUT 120 to this second drive signal (including while a drive signal is being transmitted to the PUT 120). This may be repeated any appropriate number of times and utilizing any appropriate number of frequencies and frequency values. One or more drive signals may be sequentially transmitted to the PUT 120 by the signal generator 102 and transducer 104, one or more drive signals may be simultaneously transmitted to the PUT 120 by the signal generator 102 and transducer 104, or any combination thereof.

The frequency response of the PUT 120 is transmitted to the computer 108 of the inspection tool 100 of FIG. 3. This computer 108 may be of any appropriate type and/or configuration, and is used by the inspection tool 100 to evaluate the part 120 in at least some fashion (e.g., to determine whether to accept or reject the part 120). The computer 108 may include one or more data input devices 109 of any appropriate type (e.g., keyboard, mouse, touch screen).

Generally, the part 120 is vibrated by the transducer 104 according to a predetermined signal(s), and the PUT 120 is evaluated by the resulting vibrational (e.g., whole body) response of the part 120 in the case of a resonance inspection. For instance, this evaluation may entail assessing the part 120 for one or more defects of various types, assessing whether the part 120 is at or near the end of its useful, life, assessing whether the part 120 is aging normally or abnormally, or any combination thereof. In any case, the resonance assessment module 110 may be configured to evaluate the results of a resonance inspection, for instance for purposes of determining whether the PUT 120 should be accepted or rejected by the inspection tool 100, determining whether the PUT 120 is at an end-of-life state or condition, or the like. A PUT 120 that is "accepted" by the inspection tool 100 from a resonance inspection may mean that the inspection tool 100 has determined that the part 120 may be put into service (e.g., utilized for its intended purpose(s) and/or used according to its design specifications). In one embodiment, a PUT 120 that has been accepted by the inspection tool 100 from a resonance inspection means that the tool 100 has determined that the PUT 120 is free of defects, is not in an end-of-life condition or state, is aging normally, or any combination thereof. A PUT 120 that is "rejected" by the inspection tool 100 from a resonance inspection may mean that the inspection tool 100 has determined that the PUT 120 should not be put into service (e.g., should not be utilized for its intended purpose(s) and/or should no longer be used according to its design specifications). In one embodiment, a part 120 that has been rejected by the inspection tool 100 means that the tool 100 has determined that the part 120 includes at least one defect, is at or near an end-of-life condition or state, is aging abnormally, or any combination thereof.

The computer 108 may incorporate and utilize the above-noted resonance assessment module 110 to evaluate the response of the PUT 120 to a resonance inspection. The resonance assessment module 110 may be of any appropriate configuration and may be implemented in any appropriate manner. In one embodiment, the resonance assessment module 110 includes at least one new production part sort logic 112 (e.g., logic configured to determine whether to accept or reject new production parts), at least one in-service part sort logic 114 (e.g., logic configured to determine whether to accept or reject in-service parts), along with one or more processors 116 of any appropriate type and which may be implemented in any appropriate processing architecture. The assessment of the response of the PUT 120 to the input drive signals may entail comparing the response to a library 118 utilized by the inspection tool 100. This library 118 may be stored on a computer-readable storage medium of any appropriate type or types, including without limitation by using one or more data storage devices of any appropriate type and utilizing any appropriate data storage architecture.

Figure 4:
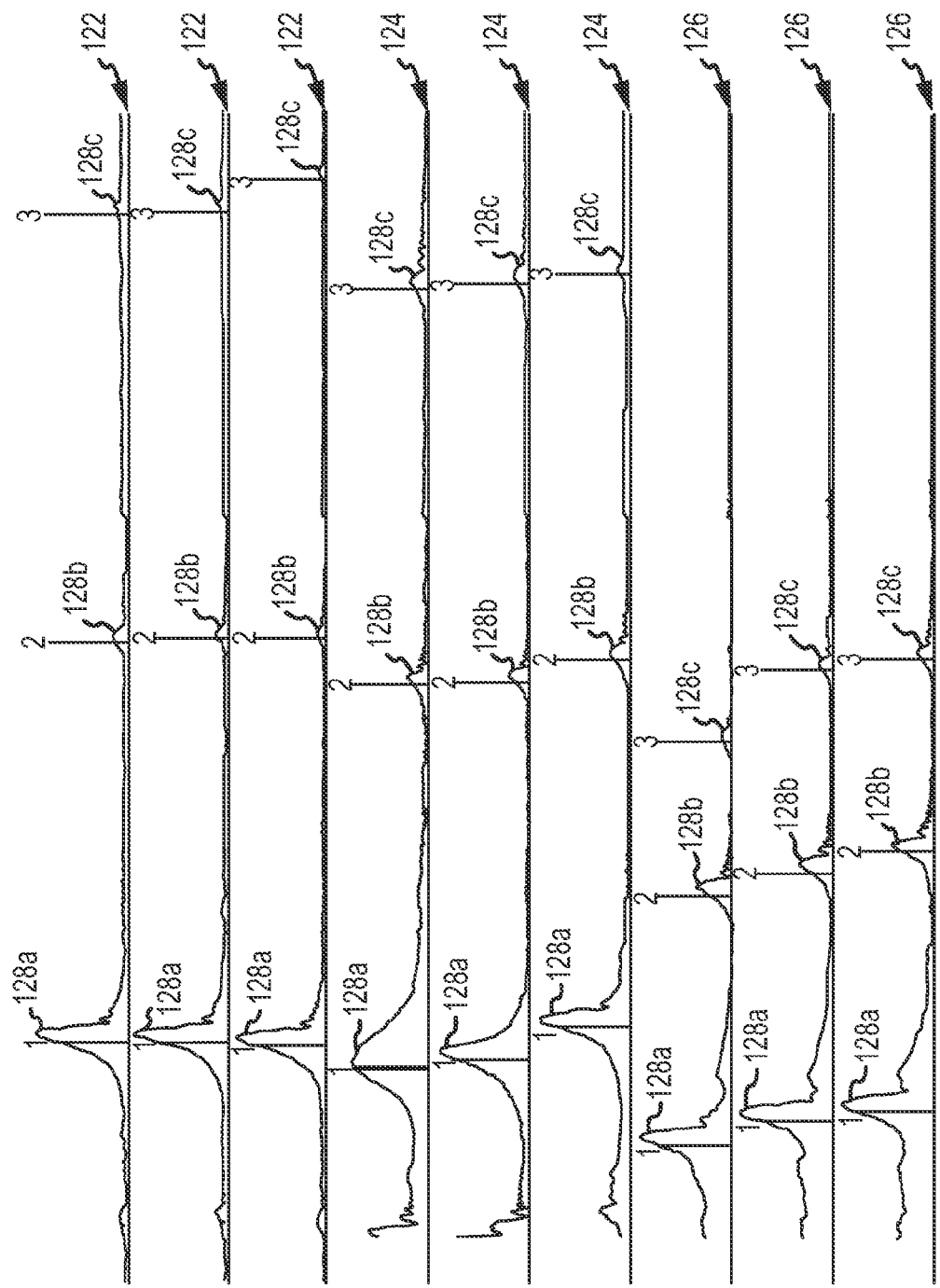
FIG. 4 presents various resonance inspection results of parts that may be included in a library utilized for conducting a resonance inspection with the inspection tool of FIG. 3.

The library 118 of the inspection tool 100 may include various types of resonance inspection results to allow the inspection tool 100 to assess a PUT 120. Generally, the resonance inspection results from the PUT 120 are compared with data in the library 118 from at least one other part that is the same as the PUT 120 in one or more respects (e.g., a PUT 120 in the form of a turbine blade will be compared to turbine blade data in the library 118; a PUT 120 in the form of a turbine blade will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the inspection tool 100. Note how the three peaks 128a, 128b, and 128c differ in at least one respect between the various spectra 122, but yet the corresponding new production part 120 is acceptable in all three instances.

The three spectra 124 shown in FIG. 4 represent the frequency response of an in-service production part 120 to a certain input frequency, and where this in-service part 120 has been accepted by the inspection tool 100. Note how the three peaks 128a, 128b, and 128c in the spectra 124 differ in at least one respect from the corresponding peaks 128a, 128b, and 128c in the spectra 122 (again, associated with a new production part 120).

The three spectra 126 shown in FIG. 4 represent the frequency response of an in-service production part 120 to a certain input frequency, and where this in-service part 120 has been rejected by the inspection tool 100. Note how the three peaks 128a, 128b, and 128c in the spectra 126 differ in at least one respect from the corresponding peaks 128a, 128b, and 128c in the spectra 124 (again, associated with an in-service part 120 that the inspection tool 100 would accept). Generally, each of the peaks 128a, 128b, and 128c in the spectra 126 has shifted to the left compared to the corresponding peaks 128a, 128b, and 128c in the spectra 122 and 124. Moreover, note the "compression" between the peaks 128a, 128b in the spectra 126 compared to the spectra 122, 124, as well as the "compression" between the peaks 128b, 128c in the spectra 126 compared to the spectra 122, 124.

Figure 5:
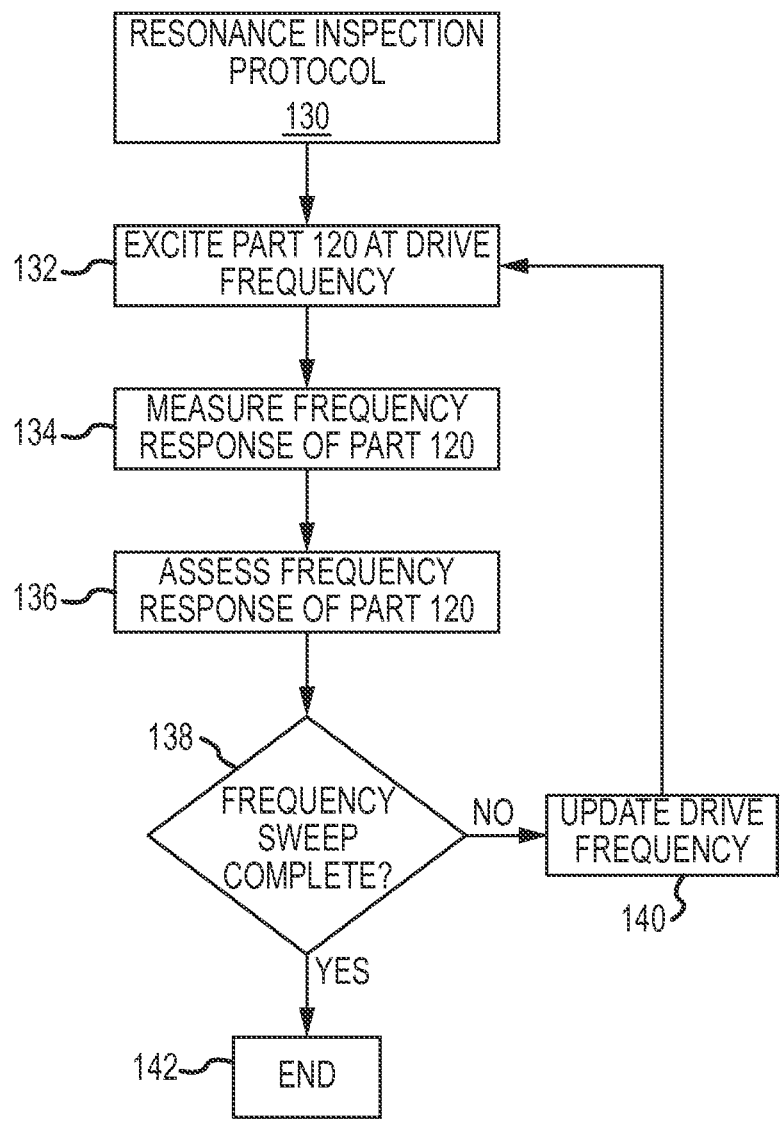
FIG. 5 is one embodiment of a resonance inspection protocol that may be utilized for conducting a resonance inspection with the inspection tool of FIG. 3.

One embodiment of a resonance inspection protocol that may be utilized by the inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 of the protocol 130 for repetition in accordance with the foregoing. Once the part 120 has been driven at each of the desired frequencies, the protocol 130 may be terminated pursuant to step 142.

Step 136 of the resonance inspection protocol 130 is again directed to assessing the response (e.g., frequency; whole body) of the part 120 (e.g., using the sort logic 112 or 114 and/or comparing the response of the part 120 to the library 118 of the inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

Figure 6:
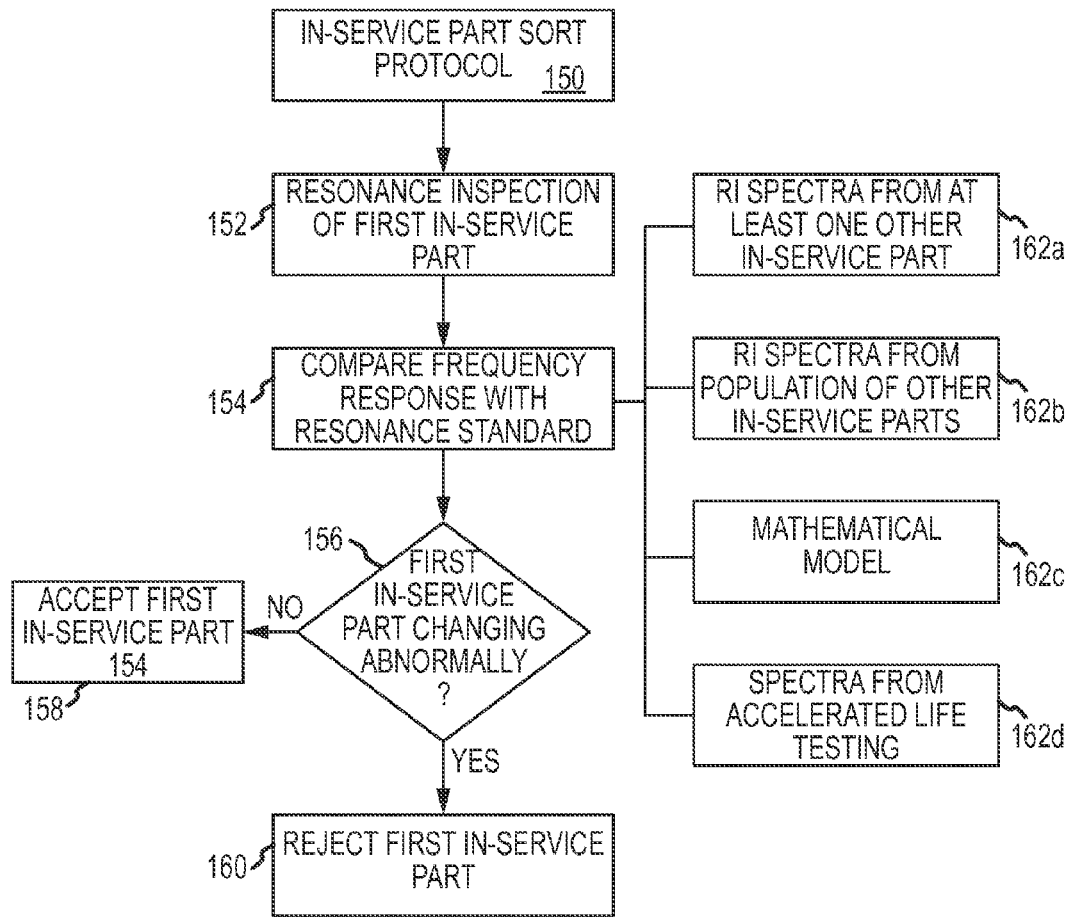
FIG. 6 is one embodiment of a sort protocol for in-service parts that may be utilized for conducting a resonance inspection with the inspection tool of FIG. 3.

One embodiment of a sort protocol for in-service parts is presented in FIG. 6 and is identified by reference numeral 150. The sort protocol 150 may be utilized by the in-service part sort logic 114 of the inspection tool 100 shown in FIG. 3, and is configured for the assessment of in-service parts. Generally, the sort protocol 150 is directed to determining whether or not an in-service part is experiencing normal changes while in service. Stated another way, the sort protocol 150 may be characterized as being directed to determining whether an in-service part is aging normally or abnormally and via a resonance inspection. Each resonance inspection of an in-service part may be conducted while the in-service part remains in an installed state or condition (e.g., in situ) for purposes of the sort protocol 150. Alternatively, each resonance inspection of an in-service part may be conducted with the in-service part being in an uninstalled state or condition (e.g., after having been removed from an assembly incorporating the same) for purposes of the sort protocol 150.

A resonance inspection of a first in-service part (e.g., part 120 shown in FIG. 3) is conducted pursuant to step 152 of the sort protocol 150 of FIG. 6 (e.g., via execution of the resonance inspection protocol 130 of FIG. 5). The frequency response of the first in-service part is compared with a resonance standard pursuant to step 154. This "resonance standard" may be incorporated by the library 118 used by the inspection tool 100 (FIG. 3) and/or may be utilized by the in-service part sort logic 114, and in any case may characterize or define what should be a "normal change" for a predetermined in-service part (e.g., to determine whether the first in-service part is changing or aging in a normal manner or fashion). That is, the comparison of step 154 is undertaken for purposes of determining whether the first in-service part is changing normally or abnormally (step 156). If the comparison with the resonance standard (step 154) determines that the first in-service part is changing abnormally, the sort protocol 150 proceeds from step 156 to step 160. A first in-service part that is changing abnormally may be rejected by the sort protocol 150 pursuant to step 160 (e.g., the first in-service part may be designated to be taken out of service). A first in-service part that is changing normally is accepted by the sort protocol 150 pursuant to step 158 (e.g., the first in-service part may be returned to service).

The resonance standard associated with step 154 may include actual and/or projected/predicted resonance inspection results. Moreover, these resonance inspection results may be from various points in time over the life cycle of a part (e.g., resonance inspection results when in the form of a new production part, resonance inspection results at or associated with 5,000 cycles of usage, resonance inspection results at or associated with 10,000 cycles of usage, resonance inspection results at or associated with 15,000 cycles of usage, and so forth). Step 156 of the sort protocol 150 may or may not take usage data (e.g., hours or cycles of operation) into account when assessing a particular in-service part. For instance, step 156 could be configured so that resonance inspection results from the in-service part being assessed via the sort protocol 150 would have to "match" data in the resonance standard having the same or comparable usage data (e.g., if the in-service part that was being assessed via the sort protocol 150 was at 10,000 cycles of usage, step 156 could be configured such that resonance inspection results from this in-service part would have to match data in the resonance standard that are also associated with 10,000 cycles of usage). Step 156 could also be configured so that resonance inspection results from the in-service part being assessed via the sort protocol 150 would only need to "match" data in the resonance standard, regardless of any associated usage data (e.g., step 156 could be configured to determine that a part at 10,000 cycles was changing normally, even though its resonance inspection results "matched" data in the resonance standard that was in fact associated with 20,000 cycles).

The resonance standard associated with step 154 of the sort protocol 150 of FIG. 6 may be of various forms. Representative resonance standards are shown in FIG. 6. The resonance standard for step 154 may be in the form of: 1) spectra from one or more other in-service parts (e.g., spectra from a resonance inspection previously conducted on one or more in-service parts other than that being inspected pursuant to the sort protocol 150 (box 162a); 2) one or more spectra from a population of other in-service parts (box 162b); 3) resonance inspection results predicted and/or derived via mathematical modeling (box 162c); and 4) spectra obtained from accelerated life testing (box 162d).

The resonance standard associated with step 154 of the sort protocol 150 could be in the form of any one or more of the type of spectra 124 shown in FIG. 4 (e.g., box 162a). If the resonance inspection results from the resonance inspection conducted pursuant to step 152 matched or complied with any of these spectra 124 in one or more respects, the in-service part could be accepted by step 158 of the sort protocol 150.

The resonance standard used by step 154 of the sort protocol 150 may be based upon a population of in-service parts (box 162b). This population of in-service parts does not need to include the first in-service part that is being assessed by the sort protocol 150. The population of in-service parts may be viewed as a "peer group" for purposes of assessing the first in-service part via the sort protocol 150 (e.g., other parts manufactured in accordance with common specifications and/or that are functionally interchangeable with the first in-service part). For instance, the resonance standard may be in the form of spectra (e.g., spectra 124 from FIG. 4) from each of a plurality of in-service parts that are within the population. If the comparison of step 154 determines that the resonance inspection results from the first in-service part (step 152) match or comply with any of these spectra from the population in one or more respects, the first in-service part may be accepted pursuant to step 158 of the sort protocol 150. The resonance standard associated with step 154 may also be in the form of an average of spectra from each of a plurality of in-service parts that are within the noted population. If the comparison of step 154 determines that the resonance inspection results (step 152) match or comply with this spectral average from the population in one or more respects, the first in-service part may be accepted pursuant to step 158 of the sort protocol 150.

The resonance standard associated with step 154 of the sort protocol 150 may also be provided by mathematical modeling (box 162c). This mathematical modeling may be used to generate resonance inspection results for various times over the life of a part that is changing normally. If the comparison of step 154 determines that the resonance inspection results (step 152) match or comply with any of these mathematically derived resonance inspection results in one or more respects, the first in-service part may be accepted pursuant to step 158 of the sort protocol 150.

The resonance standard associated with step 154 of the sort protocol 150 may also be provided by accelerated life testing (box 162d). Resonance inspection results may be acquired as a part undergoes accelerated life testing, and these resonance inspection results may be used by the resonance standard associated with step 154. If the comparison of step 154 determines that the resonance inspection results (step 152) match or comply with any of the resonance inspection results acquired during the accelerated life testing in one or more respects, the first in-service part may be accepted pursuant to step 158 of the sort protocol 150.

Figure 7:
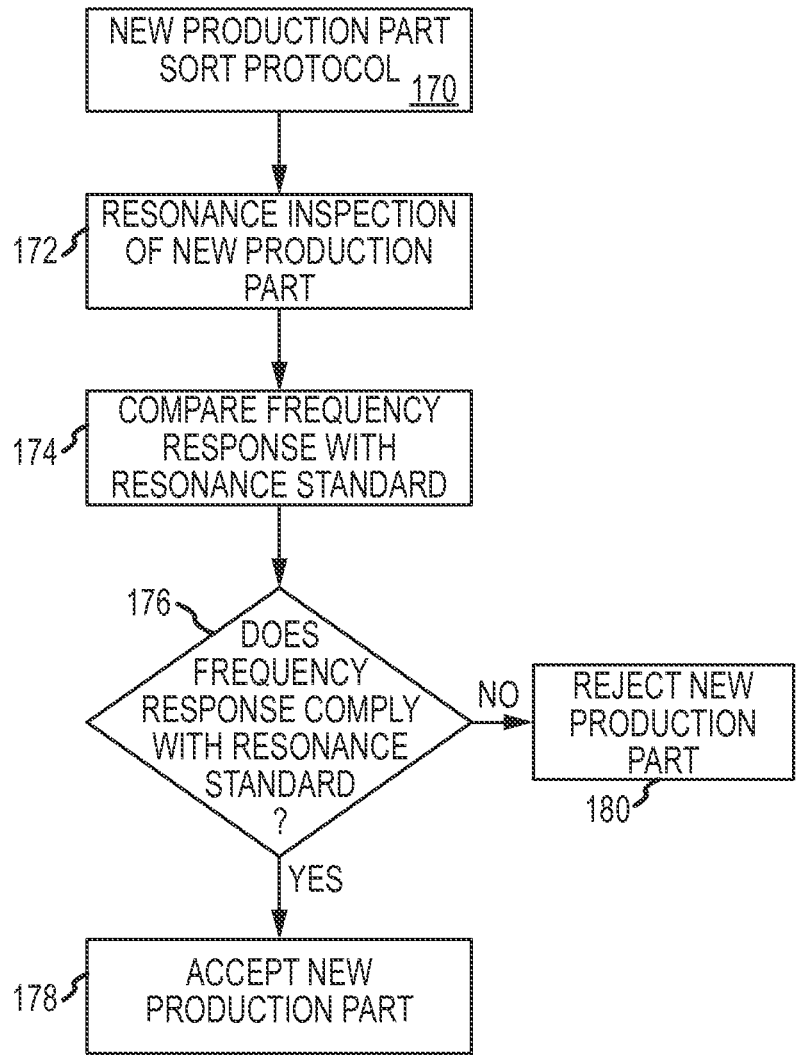
FIG. 7 is one embodiment of a sort protocol for new production parts that may be utilized for conducting a resonance inspection with the inspection tool of FIG. 3.

One embodiment of a sort protocol for new production parts is presented in FIG. 7, is identified by reference numeral 170, and may be used by the inspection tool 100 of FIG. 3. A resonance inspection of a new production part (e.g., part 120 shown in FIG. 3) is conducted pursuant to step 172 of the sort protocol 170 of FIG. 7 (e.g., via execution of the resonance inspection protocol 130 of FIG. 5). The frequency response of the new production part is compared with at least one resonance standard pursuant to step 174. Each such "resonance standard" may be incorporated by the library 118 used by the inspection tool 100 (FIG. 3) and/or may be utilized by the new production part sort logic 112, and in any case may characterize or define what should be a "normal" new production part. That is, the comparison of step 174 is undertaken for purposes of determining whether the new production part is "normal" (step 176). A new production part that does not comply with the relevant resonance standard(s) may be rejected by the sort protocol 170 pursuant to step 180 (e.g., the new production part may be designated for scrapping). A new production part that complies with the relevant resonance standard(s) is accepted by the sort protocol 170 pursuant to step 178 (e.g., the new production part may be designated for service).

The inspection tool 100 of FIG. 3 may include the above-noted surface defect assessment module 190. Generally, the surface defect assessment module 190 may be used to assess the part-under-test 120 for the existence of one or more surface defects. It is not required that the surface defect assessment module 190 be configured to identify the number and/or location of any surface defects. Instead, the surface defect assessment module 190 may simply be configured in a pass/fail mode ("pass" meaning that the surface defect assessment module 190 is accepting the part-under-test 120 based upon the lack of a surface defect trigger condition; "fail" meaning that the surface defect assessment module 190 is rejecting the part-under-test 120 based upon the existence of a surface defect trigger condition).

The surface defect assessment module 190 relies upon surface acoustical waves—a specialized type of resonance vibration that moves only at or very near the surface of the part-under-test 120. Generally speaking, surface acoustical waves penetrate the part-under-test 120 by only a single wavelength, and may be used by. The frequency of surface acoustical waves can be calculated by the following equations:

$$v_{shear} = \sqrt{(C_{66}/\rho)} \quad [1]$$

$$v_{surf} = A \cdot v_{shear}, \text{ where } 0.9 < A < 0.95 \quad [2]$$

$$f_{SAW} = v_{surf}/\lambda, \text{ where } C/\lambda = \text{integer} \quad [3]$$

where $v_{shear}$ is the shear velocity, $C_{66}$ is an elastic modulus, $\rho$ is the density, $f_{SAW}$ is the SAW mode frequency, $v_{surf}$ is the surface velocity, $\lambda$ is the wavelength of the SAW, and C is the ball circumference. For silicon nitride, the $C_{66}$ ranged from 116 to 120 GPa, and $\rho$ was approximately 3.2 g/cm³. While Equation [2] provides an estimate of the surface velocity, the actual surface velocity may be determined from empirical data.

Figure 8:
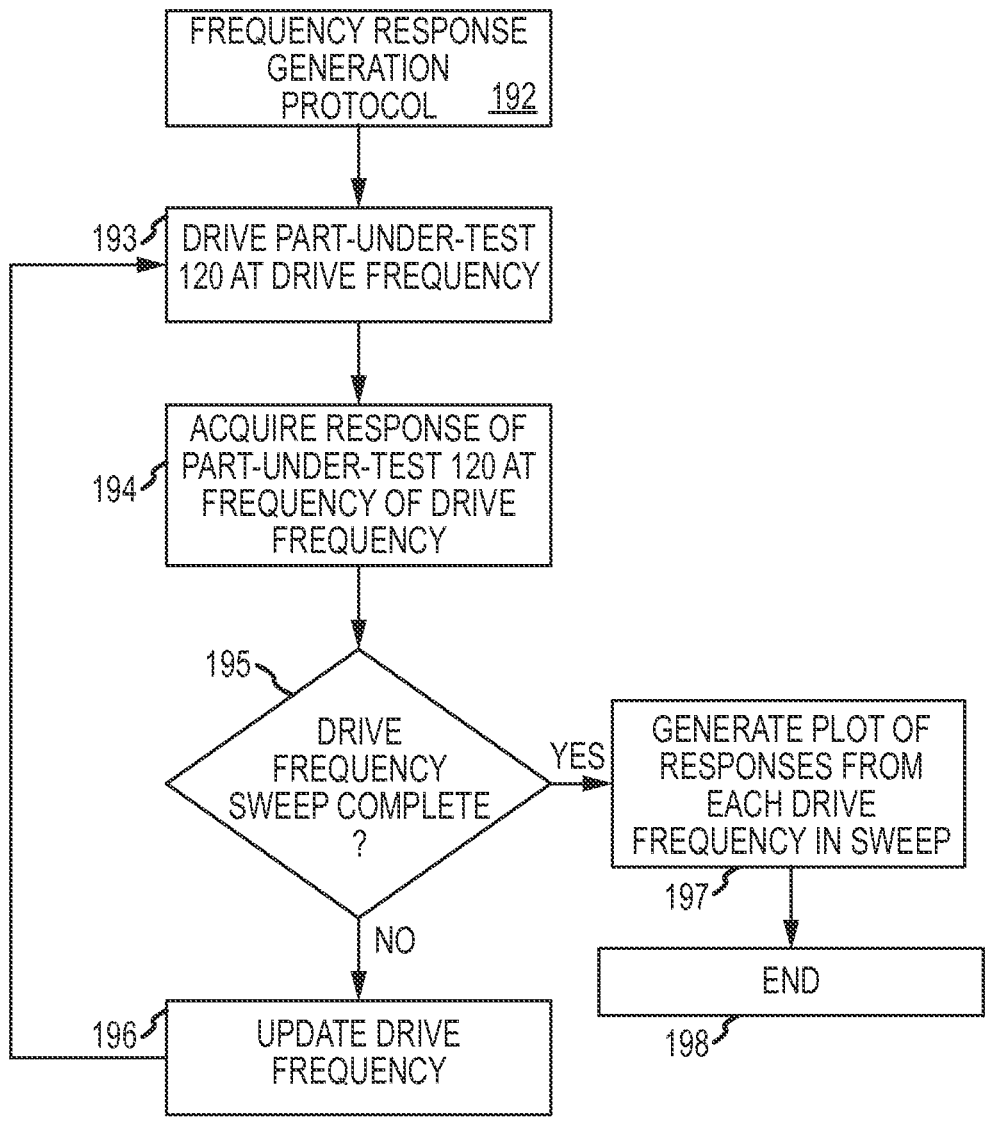
FIG. 8 is one embodiment of a protocol for generating a frequency response that may be used by surface defect inspection module of the inspection tool of FIG. 3.

A frequency response generation protocol that may be used by the surface defect assessment module 190 (FIG. 3) is illustrated in FIG. 8 and is identified by reference numeral 192. The protocol 192 may be executed by the inspection tool 100 shown in FIG. 3. In any case, the part-under-test 120 is excited by a drive frequency (step 193; e.g., utilizing the signal generator 102 and at least one transducer 104 from the inspection tool 100 of FIG. 3). A response of the part-under-test 120 is acquired at the same frequency that is used to excite the part-under-test 120 (step 194; e.g., using one or more transducers 106 and/or the transducer 104 of the inspection tool of FIG. 3). For instance, if step 193 entails inputting a drive frequency of frequency of 3,000 kHz, step 194 is directed to acquiring the response of the part-under-test 120 at a frequency of 3,000 kHz.

The part-under-test 120 may be excited through a range of frequencies to acquire data for the surface defect assessment module 190. Any appropriate range of frequencies may be used by the protocol 192 (and may be made available to the protocol 192 in any appropriate manner; e.g., hard-coded; via user input). In this regard, step 195 of the protocol 192 is directed to determining whether the desired frequency sweep has been completed. If not, the protocol 192 proceeds to step 196 where the drive frequency is updated (e.g., the drive frequency is changed; a different drive frequency is "selected"). Control of the protocol 192 is then returned to step 193 for repetition in accordance with the foregoing.

Once the part-under-test 120 has been driven at each of the desired frequencies (step 193), the frequency response generation protocol 192 proceeds from step 195 to step 197. Step 197 of the protocol 192 is directed to generating a plot of the responses (step 194) to each drive frequency used by the protocol 192 (steps 193 and 196). Once this plot (step 197) is generated, the protocol 192 may be terminated (step 198) and the plot may then be used by the surface defect assessment module 190 to determine if the part-under-test 120 includes one or more surface defects in the manner described herein.

Figure 9A:
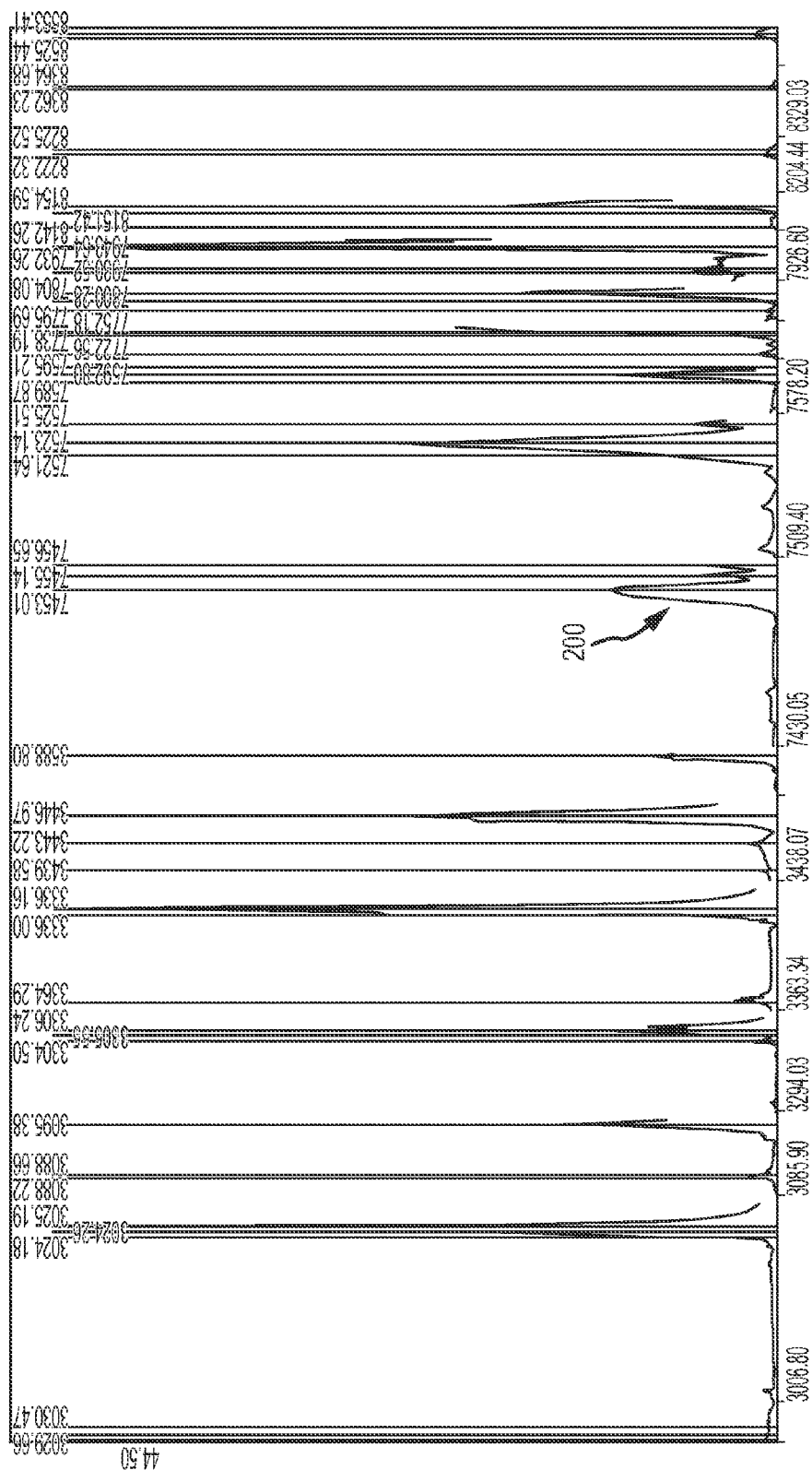
FIG. 9A is one embodiment of a frequency response that may be generated through execution of the protocol of FIG. 8.

A representative frequency response that may be generated through execution of the frequency response generation protocol 192 (FIG. 8) is presented in FIG. 9A and is identified by reference numeral 200. The frequency response 200 includes a plurality of peaks at various different frequencies. Various types of peaks may appear in the frequency response 200, including without limitation peaks that correspond with a surface acoustical wave (SAW) mode, with a resonance frequency of the part-under-test 120, or possibly with the existence of one or more surface defects on the part-under-test 120.

FIG. 9B illustrates an enlarged portion of the frequency response 200 from FIG. 9A. Here this portion of the frequency response 200 includes a single SAW mode 206, a single reference peak 204 (e.g., a resonance peak), and a single degenerate peak 210 that may be indicative of the existence of one or more surface defects on the part-under-test 120. The reference peak 204 and the SAW mode 206 define the boundaries of what may be characterized as a degeneracy assessment zone 208. The degenerate peak 210 is within the degeneracy assessment zone 208. Generally, the surface defect assessment module 190 (FIG. 3) may assess one or more degeneracy assessment zones 208 in the frequency response 200 to determine if a surface defect trigger condition exists (e.g., satisfaction of a "degenerate peak count threshold"). If such a surface defect trigger condition exists, the part-under-test 120 may have at least one surface defect, and furthermore may be characterized by the surface defect assessment module 190 as being "rejected" or as a "rejected part."

The SAW modes 206 in the frequency response 200 may be identified in any appropriate manner. For instance, the frequencies at which a SAW mode should exist may be mathematically determined, and the frequency response 200 may be assessed to look for peaks at or around these mathematically-determined frequencies. Peaks at or around these mathematically-determined frequencies may be characterized as SAW modes 206 for purposes of the surface defect assessment module 190. Other ways of identifying the SAW modes 206 in the frequency response 200 include mathematically determining the interval at which SAW modes 206 should appear, and then assessing the frequency response 200 to identify peaks that at least generally comply with this interval.

A reference peak 204 should be a peak that does not appreciably shift in response to the existence of one or more surface defects on the part under-test 120. Representative peaks that may be used as a reference peak 204 include without limitation resonance peaks, shear modes, whispering gallery modes, longitudinal modes, and the like. Reference peaks 204 in the frequency response 200 may be identified in any appropriate manner. The frequencies at which resonance peaks should exist may be mathematically determined, and the frequency response 200 may be assessed to look for peaks at or around these mathematically-determined frequencies. Reference peaks may also be identified in the frequency response 200 in the manner disclosed in co-pending U.S. Provisional Patent Application Ser. No. 61/498,656, the subject matter of which is incorporated by reference in its entirety herein.

A "degeneracy assessment zone" 208 is defined by the spacing or span between a selected SAW mode 206 and a selected reference peak 204. In one embodiment, the reference peak 204 for a given degeneracy assessment zone 208 is at a lower frequency that its corresponding SAW mode 206. The boundaries of a given degeneracy assessment zone 208 may be selected such that there are no SAW modes 206 between the reference peak 204 and SAW mode 206 that define this degeneracy assessment zone 208. In one embodiment, the SAW mode 206 of a given degeneracy assessment zone 208 is the SAW mode 206 having a frequency that is both higher than the frequency of the reference peak 204 for this degeneracy assessment zone 208 and closest to the frequency of this reference peak 204.

One or more degenerate peaks 210 may appear in a given degeneracy assessment zone 208. Degenerate peaks 210 are distinguishable from noise or the like in the frequency response 200. A peak in the frequency response 200 may be characterized as a degenerate peak 210 if it satisfies at least each of the following thresholds: 1) a predetermined amplitude threshold; 2) a predetermined threshold for the magnitude of the second derivative; and 3) a zero crossing width threshold. A peak in the frequency response 210 may also be required to have a threshold SAW mode amplitude ratio (e.g., a threshold regarding the ratio of the amplitude of the peak to the amplitude of the SAW mode 206, or vice versa), a reference peak amplitude ratio (e.g., a threshold regarding the ratio of the amplitude of the peak to the amplitude of the reference peak 204, or vice versa), or both.

FIGS. 10A/B, 11A/B, and 12A/B illustrate representative degeneracy assessment zones 208 that may appear in the frequency response 200 of a given part-under-test 120. The "A" figures in this group are representative degeneracy assessment zones 208 for a part-under-test 120 that the surface defect assessment module 190 (FIG. 3) characterizes as "accepted" (e.g., a surface defect trigger condition was not identified by the surface defect assessment module 190 for this particular part-under-test 120). The "B" figures in this group present the corresponding degeneracy assessment zone 208 (in relation to the corresponding "A" figure) for a part-under-test 120 that the surface defect assessment module 190 characterizes as "rejected" (e.g., a surface defect trigger condition was identified by the surface defect assessment module 190 for this particular part-under-test 120). None of the zones 208 overlap in any respect.

FIG. 10A presents a representative portion of a frequency response 200 that includes a single degeneracy assessment zone 208a for a part-under-test 120. This degeneracy assessment zone 208a is defined by a reference peak 204a and a SAW mode 206a. There are no degenerate peaks within the degeneracy assessment zone 208a of FIG. 10A. FIG. 10B presents this same degeneracy assessment zone 208a, but where there is now a single degenerate peak 210a in the frequency response 200. The existence of this degenerate peak 210a may be indicative of the existence of one or more surface defects on the part-under-test 120. Note the spacing between the degenerate peak 210a and each of the reference peak 204a and the SAW mode 206a, as well as the change in the SAW mode 206a between FIGS. 10A and 10B.

FIG. 11A presents a representative portion of a frequency response 200 that includes a single degeneracy assessment zone 208b for a part-under-test 120. This degeneracy assessment zone 208b is defined by a reference peak 204b and a SAW mode 206b. There are no degenerate peaks within the degeneracy assessment zone 208b of FIG. 11A. FIG. 11B presents this same degeneracy assessment zone 208b, but where there is now a single degenerate peak 210b in the frequency response 200. The existence of this degenerate peak 210b may be indicative of the existence of one or more surface defects on the part-under-test 120. Note the spacing between the degenerate peak 210b and each of the reference peak 204b and the SAW mode 206b. For instance, the spacing between the degenerate peak 210b and the reference peak 204b (FIG. 11B) is smaller than the spacing between the degenerate peak 210a and the reference peak 204a (FIG. 10B).

FIG. 12A presents a representative portion of a frequency response 200 that includes a single degeneracy assessment zone 208c for a part-under-test 120. This degeneracy assessment zone 208c is defined by a reference peak 204c and a SAW mode 206c. There are no degenerate peaks within the degeneracy assessment zone 208c of FIG. 12A. FIG. 12B presents this same degeneracy assessment zone 208c, but where there are now two degenerate peaks 210c in the frequency response 200. The existence of these two degenerate peaks 210c may be indicative of the existence of one or more surface defects on the part-under-test 120.

The surface defect assessment module 190 of FIG. 3 may be configured to characterize a part-under-test 120 as either being "accepted" or "rejected" based upon whether a surface defect trigger condition exists for this part-under-test 120. A "surface defect trigger condition" for a given part-under-test 120 may be characterized as existing when a predetermined number of degenerate peak conditions exist within one or more of the degeneracy assessment zones 208 of the frequency response 200 of this part-under-test 120. Any appropriate "predetermined number" of degenerate peak conditions may be used to define a surface defect trigger condition.

A surface defect trigger condition may be defined as existing when: 1) a predetermined number of degenerate peak conditions exist within a single degeneracy assessment zone 208 of the frequency response 200 for the part-under-test 120; 2) a predetermined number of degenerate peak conditions exist within each of a predetermined number of different degeneracy assessment zones 208 of the frequency response 200 for the part-under-test 120; 3) a predetermined number of different degeneracy assessment zones 208 of the frequency response 200 for the part-under-test 120 (including where this "predetermined number" is simply all of the degeneracy assessment zones 208 in the frequency response 200) collectively include a predetermined number of degenerate peak conditions; 4) a predetermined number of degenerate peak conditions exist within a group of degeneracy assessment zones 208, where this group includes two or more degeneracy assessment zones 208; and 5) any combination of two or more of the foregoing that are satisfied.

The surface defect assessment module 190 may be configured to equate any appropriate number of degenerate peak conditions with a surface defect trigger condition. For instance, a surface defect trigger condition may be equated with the frequency response having at least "x" number of degenerate peak conditions. A smaller number of degenerate peak conditions may be specified for a surface defect trigger condition in the case where the part-under-test 120 is a "high quality" or "critical" component. A larger number of degenerate peak conditions may be specified for a surface defect trigger condition in the case where the part-under-test is a "lower quality" or "non-critical" component. A default number of degenerate peak conditions required for a surface defect trigger condition may be utilized by the surface defect assessment module 190 (e.g., "hard-wired"), the number degenerate peak conditions required for a surface defect trigger condition may be established for the surface defect assessment module 190 by user input (e.g., through one or more data input devices 109 of the inspection system 100 of FIG. 3), or both.

Various different thresholds may be used to determine whether a degenerate peak condition exists. The surface defect assessment module 190 may be configured to equate a degenerate peak condition with the satisfaction of a spacing threshold between a degenerate peak 210 and reference peak 204 within the same degeneracy assessment zone 208. In one embodiment, this first spacing threshold is satisfied only when a degenerate peak 210 (within a degeneracy assessment zone 208) is within a predetermined distance of the reference peak 204 (associated with this same degeneracy assessment zone 208). In one embodiment, the spacing threshold is in the form of the maximum spacing that can exist between a reference peak 204 and a degenerate peak 210 within the same zone 208 in order for such a degenerate peak 210 to be characterized as defining a degenerate peak condition.

The surface defect assessment module 190 may be configured to equate a degenerate peak condition with the satisfaction of a spacing threshold between a reference peak 204 and each of two or more degenerate peaks 210 within the same degeneracy assessment zone 208. In one embodiment, this spacing threshold is satisfied only when two or more degenerate peaks 210 within a degeneracy assessment zone 208 are each within a predetermined distance of the reference peak 204 associated with this same degeneracy assessment zone 208. In one embodiment, the spacing threshold is in the form of the maximum spacing that can exist between a reference peak 204 and a degenerate peak 210 within the same zone 208 in order for such a degenerate peak 210 to be characterized as defining a degenerate peak condition.

The surface defect assessment module 190 may be configured to equate a degenerate peak condition with the satisfaction of a spacing threshold between at least one pair of degenerate peaks 210 within the same degeneracy assessment zone 208. In one embodiment, this spacing threshold is satisfied only when at least one pair of degenerate peaks 210 within a degeneracy assessment zone 208 are within a predetermined distance of each other. In one embodiment, the spacing threshold is in the form of the maximum spacing that can exist between two different degenerate peaks 210 within the same zone 208 in order for such a pair of degenerate peaks 210 to be characterized as defining a degenerate peak condition.

The surface defect assessment module 190 may be configured to equate a degenerate peak condition with the satisfaction of a spacing threshold between at least one degenerate peak 210 and a SAW mode 206 within the same degeneracy assessment zone 208. In one embodiment, this spacing threshold is satisfied only when at least one degenerate peak 210 within a degeneracy assessment zone 208 is spaced from the SAW mode 206 associated with this same degeneracy assessment zone 208 by at least a predetermined distance. In one embodiment, the spacing threshold is in the form of the minimum spacing that must exist between a SAW mode 206 and a degenerate peak 210 within the same zone 208 in order for such a degenerate peak 210 to be characterized as defining a degenerate peak condition.

Figure 13:
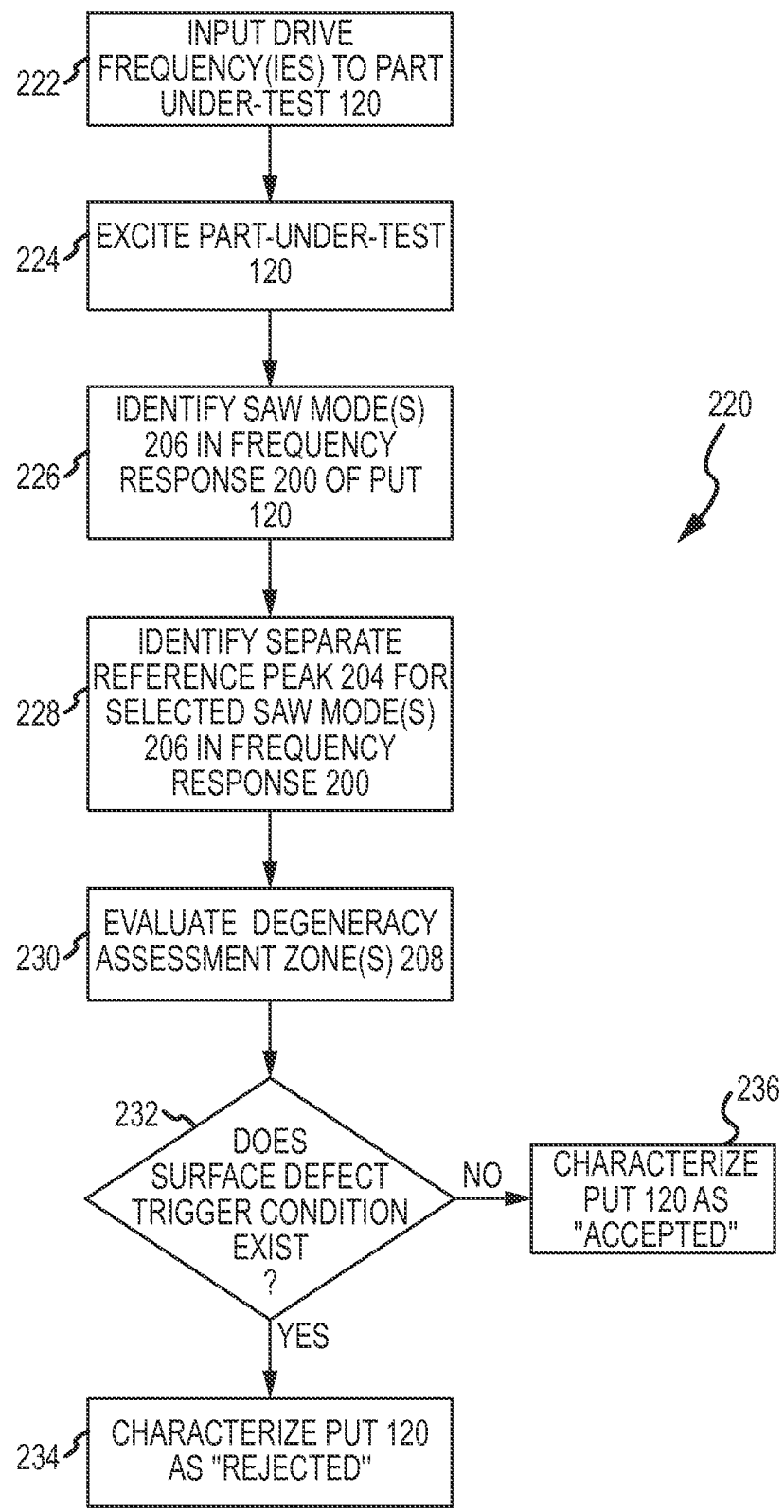
FIG. 13 is one embodiment of a surface defect assessment protocol that may be used by the surface defect inspection module of the inspection tool of FIG. 3.

FIG. 13 illustrates one embodiment of a surface defect assessment protocol 220 that may be utilized by the surface defect assessment module 190 of FIG. 3, and in accordance with the foregoing. One or more drive frequencies are input to the part-under-test 120 (step 222) and excite the part-under-test 120 (step 224). One or more SAW modes 206 are identified in the frequency response 200 of the part-under-test 120 (step 226). A separate reference peak 204 is identified for each SAW mode 206 for each degeneracy assessment zone 208 that is going to be used by the surface defect assessment module 190 (step 228) to evaluate the part-under-test 120.

One or more of the degeneracy assessment zones 208 are evaluated by the surface defect assessment module 190 (step 230). If a determination is made by surface defect assessment module 190 that a surface defect trigger condition exists (step 232), the part-under-test 120 is characterized as being "rejected" (step 234). If a determination is made by surface defect assessment module 190 that a surface defect trigger condition does not exist (step 232), the part-under-test 120 is characterized as being "accepted" (step 236).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for identifying surface defects on a part, comprising the steps of:
   exciting a part-under-test using at least one input frequency;
   identifying a first surface acoustical wave (SAW) mode in a frequency response of said part-under-test to said exciting step;
   identifying a first reference peak in said frequency response of said part-under-test to said exciting step;
   assessing a first zone extending between and including said first SAW mode and said first reference peak; and
   characterizing said part-under-test as being defective based at least in part upon an existence of a surface defect trigger condition, wherein at least part of any said surface defect trigger condition is satisfied from said first zone, wherein said surface defect trigger condition comprises having at least one degenerate peak condition within said frequency response, wherein said at least one degenerate peak condition comprises a first degenerate peak condition within said first zone, wherein said first degenerate peak condition requires an existence of at least one degenerate peak within said first zone, and wherein said assessing step in relation to said first degenerate peak condition comprises at least one of a-d as follows:
   a) assessing for an existence of a first spacing threshold between said first reference peak and a first degenerate peak within said first zone, wherein said first degenerate peak condition comprises satisfaction of said first spacing threshold;
   b) assessing for an existence of a second spacing threshold between said first reference peak and each of at least two second degenerate peaks within said first zone, wherein said first degenerate peak condition comprises satisfaction of said second spacing threshold for each of said at least two second degenerate peaks;
   c) assessing for an existence of a third spacing threshold between a pair of third degenerate peaks within said first zone, wherein said first degenerate peak condition comprises satisfaction of said third spacing threshold; and d) assessing for an existence of a fourth spacing threshold between said first SAW mode and a fourth degenerate peak within said first zone, wherein said first degenerate peak condition comprises satisfaction of said fourth spacing threshold.

2. The method of claim 1, wherein said part-under-test is of a symmetrical configuration.

3. The method of claim 1, wherein said part-under-test is of a configuration that is selected from the group consisting of a ball, sphere, cylinder, tapered roller, and right circular cylinder.

4. The method of claim 1, further comprising:
mathematically determining a frequency for said first SAW mode; and
using said frequency to identify said first SAW mode in said frequency response of said part-under-test.

5. The method of claim 1, wherein said identifying a first reference peak step comprises identifying a first resonance peak in said frequency response of said part-under-test.

6. The method of claim 1, wherein said identifying a first reference peak step comprises said first reference peak being at a lower frequency than said first SAW mode.

7. The method of claim 1, wherein said first spacing threshold comprises said first degenerate peak being within a predetermined distance of said first reference peak.

8. The method of claim 1, wherein said second spacing threshold comprises each of said at least two second degenerate peaks being within a predetermined distance of said first reference peak.

9. The method of claim 1, wherein said third spacing threshold comprises said pair of third degenerate peaks being within a predetermined distance of each other.

10. The method of claim 1, wherein said fourth spacing threshold comprises said fourth degenerate peak being spaced from said first SAW mode by at least a predetermined distance.

11. The method of claim 1, wherein said first zone has a single SAW mode in the form of said first SAW mode.

12. A method for identifying surface defects on a part, comprising the steps of:
exciting a part-under-test using at least one input frequency;
identifying a first surface acoustical wave (SAW) mode in a frequency response of said part-under-test to said exciting step;
identifying a first reference peak in said frequency response of said part-under-test to said exciting step;
assessing a first zone extending between and including said first SAW mode and said first reference peak; and
identifying a second surface acoustical wave (SAW) mode in said frequency response of said part-under-test to said exciting step;
identifying a second reference peak in said frequency response of said part-under-test to said exciting step; and
assessing a second zone extending between and including said second SAW mode and said second reference peak;
characterizing said part-under-test as being defective based at least in part upon an existence of a surface defect trigger condition, wherein at least part of any said surface defect trigger condition is satisfied from each of said first and second zones, wherein said surface defect trigger condition comprises each of said first and second zones having at least one degenerate peak condition, wherein said at least one degenerate peak condition for said first zone comprises a first degenerate peak condition, wherein said at least one degenerate peak condition for said second zone comprises a second degenerate peak condition, wherein said first and second degenerate peak conditions each require an existence of at least one degenerate peak within said first and second zones, respectively, and wherein said assessing step in relation to each of said first and second degenerate peak conditions comprises at least one of a-d as follows:

a) assessing for an existence of a first spacing threshold between said first reference peak and a first degenerate peak within said first zone, and assessing for an existence of the same said first spacing threshold between said second reference peak and a first degenerate peak within said second zone, wherein said first degenerate peak condition for said first zone comprises satisfaction of said first spacing threshold within said first zone, and wherein said second degenerate peak condition for said second zone comprises satisfaction of said first spacing threshold within said second zone;

b) assessing for an existence of a second spacing threshold between each of at least two second degenerate peaks within said first zone and said first reference peak, and assessing for an existence of the same said second spacing threshold between each of at least two second degenerate peaks within said second zone and said second reference peak, wherein said first degenerate peak condition for said first zone comprises satisfaction of said second spacing threshold for each of said at least two second degenerate peaks within said first zone, and wherein said second degenerate peak condition for said second zone comprises satisfaction of said second spacing threshold for each of said at least two second degenerate peaks within said second zone;

c) assessing for an existence of a third spacing threshold between a pair of third degenerate peaks within said first zone, and assessing for an existence of the same said third spacing threshold between a pair of third degenerate peaks within said second zone, wherein said first degenerate peak condition comprises satisfaction of said third spacing threshold within said first zone, wherein said second degenerate peak condition comprises satisfaction of said third spacing threshold within said second zone; and d) assessing for an existence of a fourth spacing threshold between said first SAW mode and a fourth degenerate peak within said first zone, and assessing for an existence of the same said fourth spacing threshold between said second SAW mode and a fourth degenerate peak within said second zone, wherein said first degenerate peak condition comprises satisfaction of said fourth spacing threshold within said first zone, wherein said second degenerate peak condition comprises satisfaction of said fourth spacing threshold within said second zone.

13. The method of claim 12, wherein said first spacing threshold comprises said first degenerate peak within said first zone being within a predetermined distance of said first reference peak, and wherein said first spacing threshold further comprises said first degenerate peak within second zone being within the same said predetermined distance of said second reference peak.

14. The method of claim 12, wherein said second spacing threshold comprises each of said at least two second degenerate peaks within said first zone being within a predetermined distance of said first reference peak, and wherein said second spacing threshold further comprises each of said at least two second degenerate peaks within said second zone being within the same said predetermined distance of said second reference peak.

15. The method of claim 12, wherein said third spacing threshold comprises said pair of third degenerate peaks within said first zone being within a predetermined distance of each other, and wherein said third spacing threshold further comprises said pair of third degenerate peaks within said second zone being within the same said predetermined distance of each other.

16. The method of claim 12, wherein said fourth spacing threshold comprises said fourth degenerate peak within said first zone being spaced from said first SAW mode by at least a predetermined distance, and wherein said fourth spacing threshold further comprises said fourth degenerate peak within said second zone being spaced from said second SAW mode by at least the same said predetermined distance.

17. A method for identifying surface defects on a part, comprising the steps of:
- exciting a part-under-test at each a plurality of different input frequencies;
- identifying a plurality of surface acoustical wave (SAW) modes in a frequency response of said part-under-test to said exciting step;
- identifying a reference peak in said frequency response of said part-under-test to said exciting step for each said SAW mode;
- assessing each zone extending between and including each said SAW mode and its corresponding said reference peak; and
- characterizing said part-under-test as being defective based upon an existence of a surface defect trigger condition, wherein said surface defect trigger condition comprises said zones collectively having a predetermined number of degenerate peak conditions, wherein each said degenerate peak condition requires an existence of at least one degenerate peak within its corresponding said zone, and wherein each said degenerate peak condition within a given said zone comprises at least one of a-d as follows:
  a) an existence of a first spacing threshold between a first degenerate peak within said given said zone and said reference peak from the same said zone;
  b) an existence of a second spacing threshold between each of at least two second degenerate peaks within said given said zone and said reference peak from the same said zone;
  c) an existence of a third spacing threshold between a pair of third degenerate peaks within said given said zone; and
  d) an existence of a fourth spacing threshold between a fourth degenerate peak within said given said zone and said SAW mode from the same said zone.

18. The method of claim 17, wherein said first spacing threshold comprises said first degenerate peak within said given said zone being within a predetermined distance of its said corresponding said reference peak from the same said zone.

19. The method of claim 17, wherein said second spacing threshold comprises each of said at least two second degenerate peaks within said given said zone being within a predetermined distance of their corresponding said reference peak from the same said zone.

20. The method of claim 17, wherein said third spacing threshold comprises said pair of third degenerate peaks within said given said zone being within a predetermined distance of each other.

21. The method of claim 17, wherein said fourth spacing threshold comprises said fourth degenerate peak within said given said zone being spaced by at least a predetermined distance from its corresponding said SAW mode from the same said zone.

* * * * *